(12) United States Patent
Chisholm et al.

(10) Patent No.: US 8,709,394 B2
(45) Date of Patent: Apr. 29, 2014

(54) ANTIMICROBIAL POLYSILOXANE MATERIALS CONTAINING METAL SPECIES

(75) Inventors: Bret Ja Chisholm, West Fargo, ND (US); Partha Majumdar, Fargo, ND (US)

(73) Assignee: NDSU Research Foundation, Fargo, ND (US)

( * ) Notice: Subject to any disclaimer, the term of this patent is extended or adjusted under 35 U.S.C. 154(b) by 831 days.

(21) Appl. No.: 12/661,902

(22) Filed: Mar. 25, 2010

(65) Prior Publication Data

US 2011/0236343 A1    Sep. 29, 2011

Related U.S. Application Data

(63) Continuation of application No. PCT/US2008/011061, filed on Sep. 24, 2008, which is a continuation-in-part of application No. 12/006,926, filed on Jan. 7, 2008, now Pat. No. 8,372,384.

(60) Provisional application No. 61/124,350, filed on Apr. 16, 2008, provisional application No. 60/995,918, filed on Sep. 28, 2007, provisional application No. 61/005,719, filed on Dec. 7, 2007.

(51) Int. Cl.
  *A61K 31/74*    (2006.01)
(52) U.S. Cl.
  USPC ...................................... 424/78.08
(58) Field of Classification Search
  None
  See application file for complete search history.

(56) References Cited

U.S. PATENT DOCUMENTS

| | | | |
|---|---|---|---|
| 4,125,491 | A | 11/1978 | Gorman |
| 4,298,543 | A | 11/1981 | Law et al. |
| 4,400,288 | A | 8/1983 | Dhanani et al. |
| 4,417,066 | A | 11/1983 | Westall |
| 4,687,813 | A | 8/1987 | Lenz et al. |
| 4,697,913 | A | 10/1987 | Kuramoto et al. |
| 4,895,964 | A | 1/1990 | Margida |
| 4,902,767 | A | 2/1990 | Roitman et al. |
| 4,910,252 | A | 3/1990 | Yonehara et al. |
| 4,933,178 | A | 6/1990 | Capelli |

(Continued)

FOREIGN PATENT DOCUMENTS

| | | |
|---|---|---|
| CA | 2 413 672 A1 | 8/2003 |
| CA | 2 621 000 | 3/2007 |

(Continued)

OTHER PUBLICATIONS

Chojnowski et al., "Polysilsesquioxanes and Oligosilsesquioxanes Substituted by Alkylammonium Salts as Antibacterial Biocides," Journal of Inorganic and Organometallic Polymers and Materials, vol. 16. No. 3, Sep. 2006, pp. 219-230.

(Continued)

*Primary Examiner* — Paul Dickinson
(74) *Attorney, Agent, or Firm* — Foley & Lardner LLP

(57) ABSTRACT

Polysiloxane-based materials, which include metal species, are provided. The polysiloxane-based compositions and materials generally include (i) amino-functional polysiloxane material and (ii) a plurality of metal species distributed within the polymeric material. Polymer based compositions in which the amino-functional polysiloxane material includes quaternary ammonium groups, e.g., tetraalkyl ammonium groups, are examples of suitable materials which may be used to form the present compositions. The metal species, which may be in an oxidized and/or neutral state, may be bonded, coordinated, chelated, suspended, and/or dispersed within the polymeric material.

19 Claims, 5 Drawing Sheets

(56) References Cited

U.S. PATENT DOCUMENTS

| | | |
|---|---|---|
| 5,001,210 A | 3/1991 | Coury et al. |
| 5,019,096 A | 5/1991 | Fox, Jr. et al. |
| 5,049,684 A | 9/1991 | Tomibe et al. |
| 5,135,742 A | 8/1992 | Halloran et al. |
| 5,203,991 A | 4/1993 | Kutsuna et al. |
| 5,225,190 A | 7/1993 | Halloran et al. |
| 5,237,082 A | 8/1993 | Leir et al. |
| 5,260,400 A | 11/1993 | Karydas |
| 5,498,644 A | 3/1996 | Reo |
| 5,602,224 A | 2/1997 | Vrckovnik et al. |
| 5,641,855 A | 6/1997 | Scherr et al. |
| 5,986,018 A | 11/1999 | Yamaguchi et al. |
| 6,030,632 A | 2/2000 | Sawan et al. |
| 6,099,897 A | 8/2000 | Sayo et al. |
| 6,124,427 A | 9/2000 | Arwood |
| 6,153,724 A | 11/2000 | Hollingsworth |
| 6,224,579 B1 | 5/2001 | Modak et al. |
| 6,369,186 B1 | 4/2002 | Branlard et al. |
| 6,387,997 B1 | 5/2002 | Grolemund et al. |
| 6,413,446 B1 | 7/2002 | Mechtel et al. |
| 6,451,437 B1 | 9/2002 | Amidaiji et al. |
| 6,458,878 B1 | 10/2002 | Tsuboi et al. |
| 6,482,912 B2 | 11/2002 | Boudjouk et al. |
| 6,500,549 B1 | 12/2002 | Deppisch et al. |
| 6,521,144 B2 | 2/2003 | Takezawa et al. |
| 6,524,564 B1 | 2/2003 | Kim et al. |
| 6,559,201 B2 | 5/2003 | Simendinger, III |
| 6,565,924 B2 | 5/2003 | Babu et al. |
| 6,716,895 B1 | 4/2004 | Terry |
| 6,723,439 B2 | 4/2004 | Amidaiji et al. |
| 6,861,493 B2 | 3/2005 | Bauer et al. |
| 6,924,116 B2 | 8/2005 | Tan et al. |
| 6,949,598 B2 | 9/2005 | Terry |
| 7,098,256 B2 | 8/2006 | Ong et al. |
| 7,141,183 B2 | 11/2006 | Hattori et al. |
| 7,179,789 B2 | 2/2007 | Patt |
| 7,204,940 B2 | 4/2007 | McDonald et al. |
| 7,235,230 B2 | 6/2007 | LeGrow et al. |
| 7,265,194 B1 | 9/2007 | Lichtenhan et al. |
| 7,297,745 B2 | 11/2007 | Amidaiji et al. |
| 7,345,131 B2 | 3/2008 | Selbertinger et al. |
| 7,378,156 B2 | 5/2008 | Terry |
| 7,449,537 B2 | 11/2008 | Boudjouk et al. |
| 7,452,956 B2 | 11/2008 | Cheng et al. |
| 7,544,722 B2 | 6/2009 | Boudjouk et al. |
| 2002/0013385 A1 | 1/2002 | Simendinger, III |
| 2002/0098214 A1 | 7/2002 | Adams et al. |
| 2002/0156223 A1 | 10/2002 | Boudjouk et al. |
| 2003/0022793 A1 | 1/2003 | Ring et al. |
| 2003/0044451 A1 | 3/2003 | McGhee et al. |
| 2003/0129421 A1 | 7/2003 | Terauchi et al. |
| 2003/0207962 A1 | 11/2003 | Oya et al. |
| 2003/0236552 A1 | 12/2003 | Roby |
| 2004/0116551 A1 | 6/2004 | Terry |
| 2005/0009985 A1 | 1/2005 | Selbertinger et al. |
| 2005/0080158 A1 | 4/2005 | Ong et al. |
| 2005/0129962 A1 | 6/2005 | Amidaiji et al. |
| 2005/0227092 A1 | 10/2005 | Yamaya et al. |
| 2006/0008613 A1 | 1/2006 | Dewinter |
| 2006/0014015 A1 | 1/2006 | Travelute et al. |
| 2006/0223969 A1 | 10/2006 | Roesler et al. |
| 2006/0252094 A1 | 11/2006 | Zhou et al. |
| 2006/0276608 A1 | 12/2006 | Lang et al. |
| 2007/0021529 A1 | 1/2007 | Boudjouk et al. |
| 2007/0032626 A1 | 2/2007 | Roesler et al. |
| 2007/0042199 A1 | 2/2007 | Chisholm et al. |
| 2007/0048344 A1 | 3/2007 | Yahiaoui et al. |
| 2007/0093618 A1 | 4/2007 | Cheng et al. |
| 2007/0112161 A1 | 5/2007 | Roesler et al. |
| 2007/0112164 A1 | 5/2007 | Roesler et al. |
| 2007/0129474 A1 | 6/2007 | Salamone et al. |
| 2007/0132949 A1 | 6/2007 | Phelan |
| 2008/0001318 A1 | 1/2008 | Schorzman et al. |
| 2008/0112920 A1 | 5/2008 | Chia et al. |
| 2008/0147019 A1* | 6/2008 | Song et al. ............. 604/265 |
| 2008/0181862 A1 | 7/2008 | Chisholm et al. |
| 2008/0199536 A1 | 8/2008 | Terry |
| 2008/0213599 A1 | 9/2008 | Webster et al. |
| 2009/0018276 A1 | 1/2009 | Boudjouk et al. |
| 2009/0111937 A1 | 4/2009 | Webster et al. |
| 2009/0143496 A1 | 6/2009 | Ziche |
| 2009/0194733 A1 | 8/2009 | Schulz et al. |
| 2009/0215762 A1 | 8/2009 | Stafslien et al. |
| 2010/0004202 A1 | 1/2010 | Chisholm et al. |
| 2010/0092530 A1* | 4/2010 | Stopek et al. ............. 424/405 |
| 2010/0204399 A1 | 8/2010 | Chisholm et al. |
| 2010/0280148 A1 | 11/2010 | Webster et al. |

FOREIGN PATENT DOCUMENTS

| | | |
|---|---|---|
| EP | 1 496 079 A1 | 1/2005 |
| JP | 2-47371 | 2/1990 |
| WO | WO 2005/030405 A2 | 4/2005 |
| WO | WO 2006/086092 A2 | 8/2006 |
| WO | WO 2006/121937 A1 | 11/2006 |
| WO | WO 2007/053163 A2 | 5/2007 |
| WO | WO 2007/108980 A1 | 9/2007 |
| WO | WO 2008/008077 A2 | 1/2008 |
| WO | WO 2009/025924 A2 | 2/2009 |

OTHER PUBLICATIONS

Tamaki et al., "Octa(aminophenyl)silsesquioxane as a Nanoconstruction Site," Journal of American Chemical Society, vol. 123, No. 49, 2001, pp. 12416-12417.
U.S. Appl. No. 60/934,093, filed Jun. 11, 2007, Webster et al.
U.S. Appl. No. 12/378,155, filed Feb. 11, 2009, Chisholm et al.
U.S. Appl. No. 12/278,049, filed Feb. 10, 2009, Stafslien et al.
U.S. Appl. No. 12/633,334, filed Dec. 7, 2009, Webster et al.
U.S. Appl. No. 11/810,696, filed Jun. 6, 2007, Webster et al.
International Search Report and Written Opinion for PCT/US2008/011061, mail date Jul. 29, 2009, 7 pages.
Abstract for Japanese Publication No. JP 04-370163, "Coating Composition," publication Date Dec. 22, 1992, 1 page.
Abstract for Japanese Publication No. JP 63-277222 A,"Curing Resin," publication Date Nov. 15, 1998, 1 page.
Abstract for Japanese Publication No. JP 11-222402, publication Date Aug. 17, 1999, Patentee or Applicant listed as Osaka Gas Co. Ltd., 1 page.
Abstract for Japanese Publication No. JP 2001-029451 (A), "Antibacterial Urethral Catheter and Manufacture of the same," Toyo Boseki et al., publication date Feb. 6, 2001, 1 page.
Abstract for JP 2000-264803, "Silver Microbide-Containing Photopolymerizable Monomer Compositions, and Solventless V- or Electron Beam-Curable Resin Compositions Containing Them," Takeuchi et al., publication date Sep. 26, 2000, 1 page.
Abstract for JP 2003-327912, "Primer Antifouling Coating Material Composition for Ship, Composite Antifouling Coating Film for Ship, Method for Forming the Composite Antifouling Coating Film, Ship Coated with the Composite Antifouling Coating Film and Antifouling Method for Outer Hull of Ship," Masuda Hiroshi et al., publication date Nov. 19, 2003, 1 page.
Abstract for JP 51-17554, "UV-Curable Antimicrobial Acrylic Coating Materials," Honda et al., publication date May 14, 1993, 1 page.
Abstract for JP 53-139653, "Marine Antifouling Material," Takamizawa Minoru et al., publication date Dec. 6, 1978, 1 page.
Abstract for JP 60-09919, "Crosslinked Urethane Acrylate Polymer Particle-Containing Antimicrobial Coatings," Honda et al., publication date Jan. 18, 1994, 1 page.
Abstract for JP 2007-246576 A, "Water Paint Composition," Matsushita et al., publication date Sep. 27, 2007, 1 page.
Abstract for JP 63-270738, "Polyamine/Polysiloxane Block Copolymer", Tezuka Yasushi et al., publication date Nov. 8, 1988, 1 page.
Adhikari et al., "Mixed Macrodiol-Based Siloxane Polyurethanes: Effect of the Comacrodiol Structure on Properties and Morphology," *Journal of Applied Polymer Science*, 2000, vol. 78, pp. 1071-1082.
Bullock et al., "Surface Science of a Filled Polydimethylsiloxane-Based Alkoxysilane-Cured Elastomer: RTV11[1]," *Journal of Colloid*

(56) References Cited

OTHER PUBLICATIONS and Interface Science, 1999, vol. 210, pp. 18-36, Article ID jcis.1998. 5856, available online at http://www.idealibrary.com.

Cassé et al., "Laboratory screening of coating libraries for algal adhesion," Biofouling, 2007, vol. 23, Nos. 3/4, pp. 267-276.

Chen et al., "Macromolecules," 1995, vol. 28, pp. 1635-1642.

Chen et al., "Solvent Effects on the Surface Composition of Poly(dimethylsiloxane)-co-Polystyrene/Polystyrene Blends," Macromolecules, 1998, vol. 31, No. 26, pp. 9328-9336.

Ekin et al., "Combinatorial and High-Throughput Screening of the Effect of Siloxane Composition on the Surface Properties of Crosslinked Siloxane-Polyurethane Coatings," J. Comb. Chem., 2007, vol. 9, No. 1, pp. 178-188.

Ekin et al., "Library Synthesis and Characterization of 3-Aminopropyl-Terminated Poly(dimethylsiloxane)s and Poly(ε-caprolactone)-b-Poly(dimethylsiloxane)s," Journal of Polymer Science: Part A: Polymer Chemistry, 2006, vol. 44, No. 16, pp. 4880-4894.

Ekin et al., "Synthesis and Characterization of Novel Hydroxyalkyl Carbamate and Dihydroxyalkyl Carbamate Terminated Poly(dimethylsiloxane) Oligomers and Their Block Copolymers with Poly(ε-caprolactone)," Macromolecules, 2006, vol. 39, No. 25, pp. 8659-8668.

Ekin et al., "Synthesis, formulation, and characterization of siloxane-polyurethane coatings for underwater marine applications using combinatorial high-throughput experimentation," J. Coat. Technol. Res., 2007, vol. 4, No. 4, pp. 435-451.

El-Hayek et al., Bacteriostatic polymer film immobilization. Journal of biomedical materials research. Part A, 2006, vol. 79 No. 4, pp. 874-881 (Plus Cover Sheet, 9 pages total).

Ha et al., Journal of Macromolecular Science, Polymer Reviews, 2005, vol. C45, 32 pgs.

Ho et al., "Polydimethylsiloxane-Urea-Urethane Copolymers with 1,4-Benzenedimethanol as Chain Extender," Macromolecules, 1993, vol. 26, No. 25, pp. 7029-7036.

Holohan et al., "Monofunctional polydimethylsiloxane oligomers for graft copolymerization," Macromol. Chem. Phys., 1994, vol. 195, No. 9, pp. 2965-2979 (Plus cover Sheet, 16 pages total).

Iojoiu et al., "Modified poly (ε-caprolactone)s and their use for drug-encapsulating nanoparticles," Journal of Polymer Science Part A: Polymer chemistry, 2004, vol. 42, No. 3, pp. 689-700.

Jiang et al., Preparation of crosslinked polystyrenes with quaternary ammonium and their antibacterial behavior Reactive & Functional Polymers 2005, vol. 62, 5 pages.

Johnston et al., "Networks from α,ω-Dihydroxpoly(dimethylsiloxane) and (Tridecafluoro-1,1,2,2-tetrahydrooctyl)triethoxysilane: Surface Microstructures and Surface Characterization," Macromolecules, 1999, vol. 32, No. 24, pp. 8173-8182.

Karal et al., "Blend of polycaprolactone-poly (dimethylsiloxane)-polycaprolactone triblock copolymer with poly(vinyl chloride) preparation and characterization," Polymer, 1997, vol. 38, No. 24, pp. 6071-6078.

Kawakami et al., "Silicone Macromers for Graft Polymer Synthesis," Polymer Journal, 1982, vol. 14, No. 11, pp. 913-917.

Lee et al., Journal of Applied Polymer Science, 2003, vol. 87, pp. 375-380.

Lenoir et al., Antimicrobial activity of polystyrene particles coated by photo-crosslinked block copolymers containing a biocidal polymethacrylate block. e-Polymers 2005, 11 pages.

Mahoney et al., Macromolecules, 2002, vol. 35, pp. 5256-5266.

Majumdar et al., "Preparation of Siloxane-Urethane Coating Having Spontaneously Formed Stable Biphasic Microtopographical Surfaces," Macromolecules, 2005, vol. 38, pp. 5875-5859.

Majumdar et al., "Thermoset Siloxane-Urethane Fouling Release Coatings," A.C.S. Symposium Series, 2007, vol. 957, pp. 61-75.

Patel et al., Macromolecules, 1988, vol. 21, pp. 2689-2696.

Pieper et al., "Combinatorial approach to study the effect of acrylic polyol composition on the properties of crosslinked siloxane-polyurethane fouling-release coatings," J. Coat. Technol. Res., 2007, vol. 4, No. 4, pp. 453-461.

Pike et al., "Water-Induced Surface Rearrangements of Poly(dimethylsiloxane-urea-urethane) Segmented Block Copolymers," Chem. Mater., 1996, vol. 8, No. 4, pp. 856-860.

Schweizer, Triclosan: a widely used biocide and its link to antibiotics. FEMS Microbiology Letters, 2001, vol. 202, No. 1, pp. 1-7 (Plus Cover Sheet, 9 pages total).

Smetankina et al., "Reactivity of organosilicon diisocyanates," XVII, Carcofunctional organosilicon compounds, Zhurnal Obshchei Khimii, 1974, vol. 44, No. 12, pp. 2638-2641.

Smith et al., Macromolecules, 1992, vol. 25, pp. 2575-2581.

Stafslien et al., "Combinatorial materials research applied to the development of new surface coatings IV. A high-throughput bacterial biofilm retention and retraction assay for screening fouling-release performance of coatings," Biofouling, 2007, vol. 23, No. 1, pp. 45-54.

Tanaka, et al., Physical Review Letters, 1992, vol. 68, No. 18, pp. 2794-2797 (Plus Figure, 5 pages total).

Tang et al., "Anti-inflammatory properties of triblock siloxane copolymer-blended materials," Biomaterials, 1999, vol. 20, pp. 1365-1370.

Tezuka et al., "Environmentally induced Macromolecular Rearrangement on the Surface of Polyurethane-Polysiloxane Block Copolymers," J. Chem. Soc. Paraday Trans., 1991, vol. 87, pp. 147-152.

Tezuka et al., "Environmentally Induced Macromolecular Rearrangement on the Surface of Polyurethane-Polysiloxane Graft Copolymers," Journal of Colloid and Interface Science, May 1990, vol. 136, No. 2, pp. 408-414.

Thomas et al., "Silicones Containing Pendant Biocides for Antifouling Coatings," Biofouling, vol. 20, Nos. 4/5, Aug./Oct. 2004, pp. 227-236.

Wynne et al., ACS Symposium Series, 1994, vol. 572, pp. 64-80 (Plus Cover Sheet, 18 pages total).

Yilgor et al., "Novel triblock siloxane copolymer: Synthesis, characterization, and their use as surface modifying additives," Journal of Polymer Science Part A: Polymer chemistry, 1989, pp. 3673-3690.

Zhuang et al., "Determination of the Distribution of Poly(dimethylsiloxane) Segment Lengths at the Surface of Poly[(dimethylsiloxane)-urethane]-Segmented Copolymers by Time-of-Flight Secondary Ion Mass Spectrometry," Macromolecules, 1997, vol. 30, No. 4, pp. 1153-1157.

* cited by examiner

| COATINGS DAYS IN AgNO₃ soln(5%) | S-15 WITH QAS | S-15 WITHOUT QAS | S-27 WITH QAS | S-27 WITHOUT QAS | S-35 WITH QAS | S-35 WITHOUT QAS |
|---|---|---|---|---|---|---|
| 0 | ⊂⊃ | ⊂⊃ | ⊂⊃ | ⊂⊃ | ⊂⊃ | ⊂⊃ |
| 1 | ✚ | ⊂⊃ | ✚ | ⊂⊃ | ✚ | ⊂⊃ |
| 4 | ✚ | ⊂⊃ | ✚ | ⊂⊃ | ✚ | ⊂⊃ |
| 6 | ✚ | ⊂⊃ | ✚ | ⊂⊃ | ✚ | ⊂⊃ |

ZONE OF INHIBITION = ✚

NO ZONE OF INHIBITION = ⊂⊃

US 8,709,394 B2

ANTIMICROBIAL POLYSILOXANE MATERIALS CONTAINING METAL SPECIES

CROSS REFERENCE TO RELATED APPLICATIONS

This application is a continuation of International Application PCT/US2008/011061, filed on Sep. 24, 2008, entitled "Antimicrobial Polysiloxane Materials Containing Metal Species," which claimed the benefit under 35 U.S.C. §119(e) of U.S. Provisional Application Ser. No. 61/124,350, filed on Apr. 16, 2008 (entitled "Antimicrobial Polysiloxane Materials Containing Metal Species"), U.S. Provisional Application Ser. No. 60/995,918, filed on Sep. 28, 2007 (entitled "Quaternary Ammonium Functionalized Cross-Linked Polyalkylsiloxanes with Anti-Fouling Activity"), and U.S. Provisional Application Ser. No. 61/005,719, filed on Dec. 7, 2007 (entitled "Quaternary Ammonium Functionalized Cross-Linked Polyalkylsiloxanes with Anti-Fouling Activity"); and which is a continuation-in part and claims priority under 35 U.S.C. §§120 of U.S. application Ser. No. 12/006,926, filed on Jan. 7, 2008 (entitled "Quaternary Ammonium Functionalized Cross-Linked Polyalkylsiloxanes with Anti-Fouling Activity"); the disclosures of which are herein incorporated by reference in their entirety.

GOVERNMENT RIGHTS STATEMENT

The U.S. Government has a paid-up license in this invention and the right in limited circumstances to require the patent owner to license others on terms as provided by Grant Nos. N00014-05-1-0822 and N00014-06-1-0952, awarded by the Department of Defense Office of Naval Research.

BACKGROUND

Quaternary ammonium salts (QASs) have been known and widely used for more than half a century as disinfectants. It is now accepted that they exert their biocidal activity by an electrostatic mechanism with the cell wall of bacteria. Surfaces coated with QAS-containing polymers retained their activity over a longer period of time. Polysiloxanes with QAS groups are attractive as biocidal polymers as polysiloxanes have high chain flexibility which allows easier contact between microorganisms and QAS. QASs with long alkyl chains are good candidates for this function, as structure, density, and distribution of QASs in the polymer matrix may affect their biocidal activity. A typical coating formulation containing QAS has large number of variables including: the types of QASs; levels of QAS addition; molecular weight of polysiloxanes; levels of catalyst; and the amount of crosslinker.

Silver is another widely-used antimicrobial agent, and it is known that silver species exert their biocidal activity through a leaching mechanism. Previous work has shown that the addition of silver nanoparticles or silver salts to silicone coating solutions generally results in poor dispersion of the silver nanoparticles or silver salts in the silicone coating. This may be due to the nonpolar nature of silicones.

SUMMARY

The present application relates to polysiloxane materials, which include metal species. The present compositions and materials generally include (i) amino-functional polysiloxane material and (ii) a plurality of metal species distributed within the polymeric material. Polymer based compositions in which the amino-functional polysiloxane material includes quaternary ammonium groups, e.g., tetraalkyl ammonium groups, are examples of suitable materials which may be used to form the present compositions.

As employed herein, the "metal species distributed within the polymer" includes metal species which may be bonded, coordinated, chelated, suspended, and/or dispersed within the polymeric material. The metal species may be in an oxidized and/or neutral state. The metal species may be at least partially present in a cationic state, e.g., as metal (I)-(VII) cations. For example, at least a portion of the metal species may be present in the form of a metal salt (e.g., as an organic soluble metal salt and/or an water soluble metal salt). Silver species such as soluble silver salts, e.g., silver nitrate, and/or nanoparticulate metallic silver (zero valent silver) are one example of suitable metal species which may be employed in the present polymer-based composite materials. Other suitable metal species may include suitable forms of zinc, cadmium, mercury, antimony, gold, aluminum, copper, platinum, titanium and/or palladium species. For example, in certain embodiments the present polysiloxane materials may include titanium species in the form of titanium dioxide ("TiO2"), e.g., in antimicrobially effective amounts. Certain embodiments may include mixtures of silver nanoparticles and platinum species (e.g., platinum nanoparticles). Such a combination since may form a galvanic couple that facilitates the generation of silver cations.

The metal species may be homogenously distributed throughout the polymeric material. In other embodiments, the metal species may be more concentrated in a portion or region of the polymeric material, e.g., in an outer portion of a coating layer formed from the amino-functional polysiloxane material. In many suitable embodiments of the polymer-based material, the metal species are present as a uniformly dispersed mixture at the molecular or ionic level in the polymeric material, i.e., as a solution of the metal species in the polymeric material. In other embodiments, the metal species may be present as nanoparticles of the zero valent (metallic) state of the metal species. In certain embodiments, the metal species are present in a sufficient amount to provide anti-microbial activity against Gram-negative bacteria and/or Gram-positive bacteria. In certain embodiments, the metal species may be present in a sufficient amount to provide a semi-conductive or conductive polymer-based material.

The present polysiloxane materials typically do not include more than about 5 wt. % of the metal species (based on the total weight of a coating composition including the material) and, in many instances, no more than about 3 wt. %. For example, polysiloxane materials which include more than about 2 wt. % of a metal species, such as silver ions and/or silver nanoparticles, may exhibit useful properties as antimicrobial coatings. Such coatings may quite suitably contain about as little as about 0.05 wt. % of a metal species, such as silver ions and/or silver nanoparticles. Where the metal species are predominantly in an outer layer of a coating, e.g., where the metal species are introduced by exposure of a coating formed from the present polymer-based compositions to a solution containing the metal species, antimicrobial activity may be achieved with coatings having about 0.05 to about 0.2 wt. % of the metal species, based on the total weight of the coating.

The amino-functional polysiloxane material typically includes quaternary amino groups. In other embodiments the amino-functional polysiloxane may include amino groups which are protonated to form a quaternary ammonium salt, e.g., the protonated form of a trialkyl substituted amino group. In some embodiments, the amino-functional polysiloxane may include primary and/or secondary amino groups which may be protonated to form a quaternary ammonium salt.

Examples of suitable amino-functional polysiloxane material include a polymeric material prepared by reacting a mixture which includes alkoxysilyl functionalized amine and silanol terminated polysiloxane. For example, suitable siloxane based polymers may be formed by reacting a mixture which includes alkoxysilyl functionalized quaternary amine and silanol terminated polysiloxane. In other embodiments, the amino-functional polysiloxane material may include a polymeric material prepared by reacting a mixture which includes alkoxysilyl functionalized polyamine and silanol terminated polysiloxane. Other examples of amino-functional polysiloxanes which may be employed in present metal species containing polymer-based composites are described herein. It is often desirable to employ a cross-linked form of the polymer-metal species composite materials. These may be formed by reacting a mixture which includes an amino functional polysiloxane, a silanol-containing polysiloxane and a suitable crosslinking agent, e.g., a polyhydroxy-functional compound and/or a polyalkoxysilane compound.

DETAILED DESCRIPTION

Figure 1:
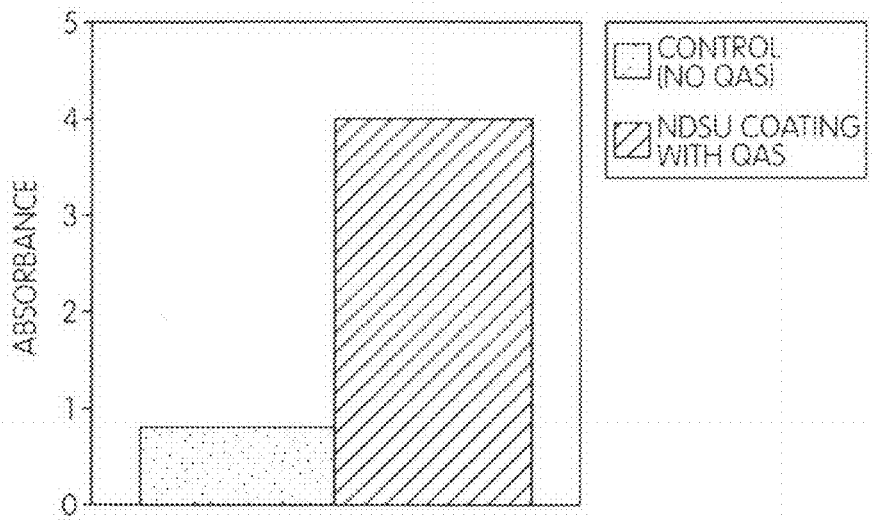
FIG. 1 shows turbidity measurements of siloxane-based coating solutions containing 1 weight percent silver nanoparticles 24 hours after vortex mixing.

Generally, the present compositions and materials include (i) amino-functional polysiloxane material and (ii) a plurality of metal species distributed within the polymeric material. As noted above, the polymer composite may include a second antimicrobial agent, in a form that is blended into and/or bonded to the polysiloxane. Examples of suitable antimicrobial agents which may be included in the present compositions and materials include chlorhexidine and/or chlorinated phenols, such as triclosan. Other examples of suitable antimicrobial agents include gramicidin, polymixin, norfloxacin, sulfamylon, polyhexamethylene biguanide, alexidine, levofloxacin, minocycline, iodine, benzalkonium chloride and/or rifampicin. In certain embodiments, the present polymer composite may also include an antifungal agent, such as miconazole and/or ciclopiroxolamine. In other embodiments, the present polymer composite may include other antifungal agents capable of suppressing the growth of and/or killing yeasts.

In some embodiments, suitable amino-functional polysiloxanes may include polyalkylsiloxanes formed by reacting a mixture which includes alkoxysilyl functionalized amine and silanol terminated polysiloxane. Such suitable siloxane based polymers may be formed by reacting a mixture which includes alkoxysilyl functionalized quaternary amine and silanol terminated polysiloxane. In other embodiments, the amino-functional polysiloxane material may include a polymeric material prepared by reacting a mixture which includes alkoxysilyl functionalized polyamine and silanol terminated polysiloxane. Examples of suitable quaternary ammonium functionalized polysiloxanes are disclosed in U.S. patent application Ser. No. 12/006,926, filed on Jan. 7, 2008, and entitled "Quaternary Ammonium Functionalized Cross-linked Polysiloxanes with Anti-fouling Activity," the entire contents of which are herein incorporated by reference. Examples of suitable polysiloxanes cross-linked via reaction with a polyamine cross linking agent are disclosed in U.S. patent application Ser. No. 11/429,923, entitled "Anti-Fouling Materials Containing Cationic Polysiloxanes," (published as U.S. Patent Application No. 2007/0042199), the entire contents of which are herein incorporated by reference.

In one embodiment, the amino functional polysiloxane material may be prepared by reacting a mixture which includes alkoxysilyl functionalized quaternary amine and silanol terminated polysiloxane. The mixture may further comprise a tetra-functional acyloxysilane and/or alkoxysilane, e.g., an alkyltriacyloxysilane. In other embodiments, the mixture may comprise a trifunctional silane, e.g., in which the reactive functionality is selected from the group consisting of alkoxysilane, acyloxysilane, silazane, halosilane, and ketoxime-based silane. The alkoxysilyl functionalized quaternary amine may include a compound of the structure

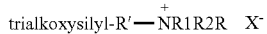

wherein R1 and R2 are lower alkyl, R' is alkylene, R may be an n-alkyl group having 5 to 25 carbon atoms, and X is a halide. In other embodiments, the alkoxysilyl functionalized quaternary amine may include a bis-(alkoxysilyl functionalized)-quaternary amine, e.g., where the quaternary amino functional group is a tetraalkyl quaternary amino group. In some embodiments, the mixture used to produce the quaternary amino functionalized cross-linked polysiloxane may also include a filler, such as silica. For example, suitable cross-linked polysiloxanes may be prepared by reacting a mixture which includes alkoxysilyl functionalized quaternary amine and silanol terminated polysiloxane. In certain embodiments, the mixture may also include up to about 25 wt. % and, more suitably about 5 to 15 wt. % silica.

In another embodiment, the polysiloxane material comprises a cross linked copolymer which is prepared by cross linking a copolymer (random or block) using a polyamine or polyhalide functionalized material where the copolymer has the formula:

is an amino group, the material that is used to cross link the copolymer is a polyhalide), or an end cap group;

$L^1$, $L^2$, and $L^3$ are linking groups;

$R^1$, $R^2$, $R^3$, and $R^{10}$ are independently $C_1$-$C_{10}$ alkyl, cyclopentyl, cyclohexyl, benzyl, toluoyl, xylyl or phenyl;

$R^4$ is hydrogen, $C_1$-$C_{10}$ alkyl, cyclopentyl, cyclohexyl, benzyl, toluoyl, xylyl, or phenyl;

$R^5$ is $C_1$-$C_{10}$ alkyl, cyclopentyl, cyclohexyl, benzyl, toluoyl, xylyl, phenyl, or a cross linking group;

$R^7$ is hydrogen, $C_1$-$C_{10}$ alkyl, cyclopentyl, cyclohexyl, benzyl, toluoyl, xylyl, phenyl, or a cross linking group;

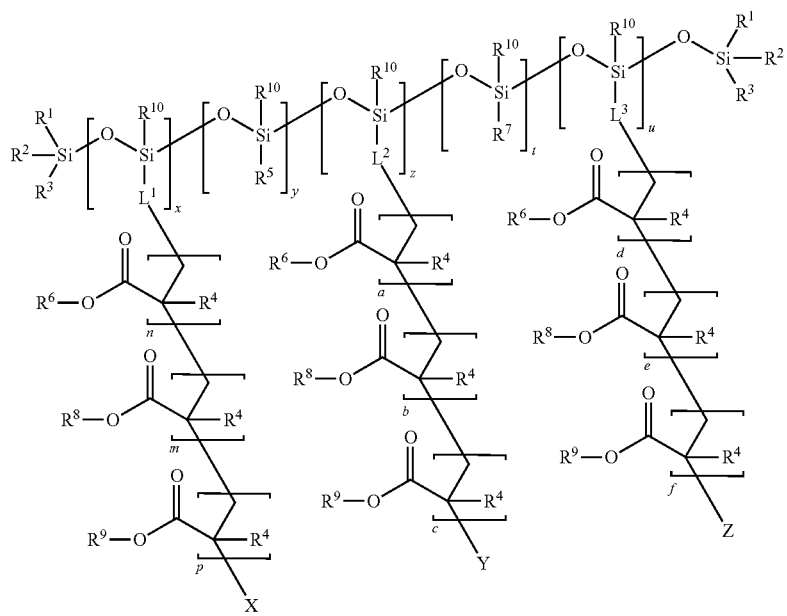

wherein x is an integer from 0 to 100, 1 to 50, or 2 to 10;
y is an integer from 0 to 100, 1 to 25, or 2 to 10;
z is an integer from 0 to 100, 1 to 50, or 2 to 10;
t is an integer from 0 to 100, 1 to 25, or 2 to 10;
u is an integer from 0 to 100, 1 to 50, or 2 to 10;
x+y+z+t+u is at least 5, 10, 50, 100 or between 25-250, or 50-200;
n is an integer from 0 to 50, 5 to 40, or 10 to 30;
m is an integer from 0 to 50, 5 to 40, or 10 to 30;
p is an integer from 0 to 50, 5 to 40, or 10 to 30;
a is an integer from 0 to 50, 5 to 40, or 10 to 30;
b is an integer from 0 to 50, 5 to 40, or 10 to 30;
c is an integer from 0 to 50, 5 to 40, or 10 to 30;
d is an integer from 0 to 50, 5 to 40, or 10 to 30;
e is an integer from 0 to 50, 5 to 40, or 10 to 30;
f is an integer from 0 to 50, 5 to 40, or 10 to 30;
X is a halide, an amino group (if X is a halide, the material that is used to cross link the copolymer is a polyamine or if X is an amino group, the material that is used to cross link the copolymer is a polyhalide), or an end cap group;
Y is a halide, an amino group (if Y is a halide, the material that is used to cross link the copolymer is a polyamine or if Y is an amino group, the material that is used to cross link the copolymer is a polyhalide), or an end cap group;
Z is a halide, an amino group (if Z is a halide, the material that is used to cross link the copolymer is a polyamine or if Z $R^6$, $R^8$, and $R^9$ include independently a biocidal group that is toxic to organisms that cause fouling in an aqueous environment; a fouling release group; a texturizing group; or combination thereof.

In some embodiments, the present compositions and materials may include (i) amino-functional polysiloxane material and (ii) a plurality of silver species distributed within the polymeric material. In some embodiments, the silver species may be homogenously distributed throughout the polymeric material. In other embodiments, the silver species may be more concentrated in an outer portion of a coating layer formed from the amino-functional polysiloxane material. In many suitable embodiments of the polymer-based material, the silver species are present as a uniformly dispersed mixture at the molecular or ionic level in the polymeric material, i.e., as a solution of the silver species in the polymeric material. In certain embodiments, the silver species are present in a sufficient amount to provide anti-microbial activity against Gram-negative bacteria and/or Gram-positive bacteria. For example, in certain embodiments polymeric materials which contain no more than about 1.0 wt. % silver nanoparticles may exhibit antimicrobial activity against bacteria, such as *E. coli* and/or *S. aureus*. In certain other embodiments, the silver species may be present in a sufficient amount to provide a semi-conductive or conductive polymer-based material.

As employed herein, the "silver species distributed within the polymer" includes silver species which may be bonded, coordinated, chelated, suspended, and/or dispersed within the polymeric material. The silver species may be in an oxidized and/or neutral state. The silver species may be at least partially present in a cationic state, e.g., as silver(I) cations. For example, at least a portion of the silver species may be present in the form of a silver salt (e.g., as an organic soluble silver salt and/or a water soluble silver salt). Suitable organic soluble silver salts may include, e.g., silver sulfadiazine, silver acetate, silver benzoate, silver citrate, silver lactate, silver tartrate, or other silver carboxylate salts. Other examples of suitable silver salts may include water soluble silver salt, such as silver nitrate.

EXAMPLES

The following illustrative examples are presented to illustrate the present polymer-based composite materials, coatings and methods to assist one of ordinary skill in making and using the same. The examples are not intended in any way to otherwise limit the scope of the invention described herein.
Materials Used for the Examples:

2,000 g/mole silanol-terminated polydimethylsiloxane (PDMS-2K, S-15), 18,000 g/mole silanol-terminated polydimethylsiloxane (PDMS-18K, S-27), 49,000 g/mole silanol-terminated polydimethylsiloxane (PDMS-49K, S-35), octadecyldimethyl(3-trimethoxysilylpropyl) ammoniumchloride (C18-QAS, SIO 6620), n-octadecyltrimethoxysilane (C18-Xlink, SIO6645), and methyltriacetoxysilane (SIM6519, MeAc) were purchased from Gelest. Silver nanoparticles GA-AgNP (0.45 mg/ml of Ag conc.) and S1-AgNP (0.45 mg/ml of Ag conc.) were obtained from University of Missouri. 1.0 M tetrabutylammoniumfluoride (TBAF) in tetrahydrofuran, Levofloxacin, silver nanopowder (<100 nm), and silver nitrate were obtained from Aldrich. 24-well polystyrene array plates and toluene were obtained from VWR. 4-Methyl-2-pentanone was purchased from Alfa Aesar. Intergard 264 epoxy primer was obtained from International Marine Coating. Dowcorning® RTV sealant 734 was obtained from Dowcorning. Luria-Bertani broth (LBB), tryptic soy broth (TSB), glycerol, Luria-Bertani agar (LBA), tryptic soy agar (TSA), 33% glacial acetic acid, 0.3% crystal violet in alcohol solution (CV), 10× phosphate-buffered saline (PBS), dextrose monohydrate and magnesium sulfate were purchased from VWR International (West Chester, Pa.). BacTiter-Glo™ microbial cell viability kit was purchased from Promega Corporation (Madison, Wis.). Aqueous solution of silver nitrate, stock solutions of 80 wt % PDMS 49K in toluene, and 50 mmolar TBAF in 4-methyl-2-pentanone (Cat sol) were prepared while all other reagents were used as received.

Example 1

A standard siloxane coating solution containing 1.0 weight percent silver nanoparticles and a comparable coating solution that contained the QAS functionality were prepared. Turbidity measurements were made 24 hours after vortex mixing the two coatings solutions. As shown in FIG. 1, the solution including the QAS functional siloxane was much more turbid (higher absorbance value) than the solution which merely included the control polymer (silicone which had not been functionalized to include QAS groups bonded to the polymeric material). The higher turbidity of the QAS-functional siloxane shows that the QAS functional polysiloxane enables a much better dispersion of the silver nanoparticles.

Example 2

Materials: S-15 (MW=2000), S-27 (MW=18000), and S-35 (MW=49000), are three silanol-terminated polydimethylsiloxanes (silanol-PDMS) that were used in coating formulations. Coatings with tethered QAS were prepared by reacting silanol-PDMS with trimethoxy functional quaternary ammonium salts with 18 alkyl chain (QAS) in the presence of methyltriacetoxy silane and tetrabutylammonium fluoride (TBAF) catalyst. Aqueous solution of silver nitrate, stock solutions of 80 wt % PDMS 49K in toluene, and 50 mmolar TBAF in 4-methyl-2-pentanone (Cat sol) were prepared while all other reagents were used as received. Coatings were prepared by deposition of the coating solution immediately after mixing over primed aluminum discs. Control coatings, i.e. coatings without QAS, were prepared by replacing QAS with a trimethoxy functional 18 alkyl chain crosslinker.

Discs coated with QAS-tethered polysiloxane were immersed in 5% aqueous silver nitrate solution for different periods of time. After drying, the antimicrobial activity of the coatings against Gram-negative bacterium, E. coli, and Gram-positive bacterium, S. aureus, were evaluated. The results, shown in FIGS. 2 and 3, demonstrate that discs coated with QAS tethered polysiloxane had zones of inhibition of bacterial growth surrounding them, as well as no bacterial growth on the coated disc surface for both E. coli and S. aureus. In contrast, polysiloxane coatings without bound QAS had no zone of inhibition and bacterial growth for both E. coli and S. aureus was observed on the coated disc surface.

Example 3

PDMS-QAS Coatings with Releasable Silver Ions

Materials: 2,000 g/mole silanol-terminated polydimethylsiloxane (PDMS 2K, S-15), 18,000 g/mole silanol-terminated polydimethylsiloxane (PDMS 18K, S-27), 49,000 g/mole silanol-terminated polydimethylsiloxane (PDMS 49K, S-35), octadecyldimethyl(3-trimethoxysilylpropyl) ammoniumchloride (C18-QAS, SIO 6620), n-octadecyltrimethoxysilane (C18-Xlink, SIO6645), and methyltriacetoxysilane (SIM6519, MeAc) were purchased from Gelest. 1.0 M tetrabutylammoniumfluoride (TBAF) in tetrahydrofuran and silver nitrate were obtained from Aldrich. Toluene was obtained from VWR. 4-Methyl-2-pentanone was purchased from Alfa Aesar. Aqueous solution of silver nitrate, stock solutions of 80 wt % PDMS 49K in toluene, and 50 mmolar TBAF in 4-methyl-2-pentanone (Cat sol) were prepared while all other reagents were used as received.

Coating preparation: Coating with tethered QAS was prepared by mixing 3.5 g of PDMS, 0.579 g of C-18 QAS, 0.525 g of MeAc, and 0.525 g of cat sol in a 20 ml vial. After through mixing, depositions were made over primed aluminum discs. Coatings were cured for 24 h at room temperature, followed by an additional 24 h in an oven at 50° C. Control coating, i.e. coating without tethered QAS was prepared by mixing 3.5 g of PDMS, 0.26 g of C18-Xlink, 0.525 g of MeAc, and 0.525 g of cat sol in a 20 ml vial. After through mixing, depositions were made over primed aluminum discs. Coatings were cured for 24 h at room temperature, followed by an additional 24 h in an oven at 50° C. Cured coatings were immersed in aqueous silver nitrate solution of different concentrations for different time period. After immersion, coatings were rinsed with water and dried at room temperature for 24 h.

Results and Discussion

Figure 2:
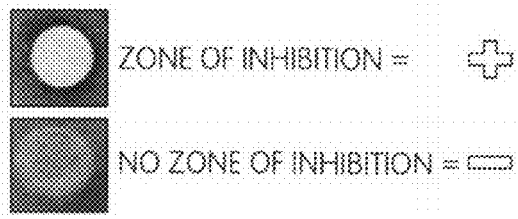
FIG. 2 shows the effect of siloxane-based coatings, both with and without quaternary ammonium groups after treatment of the coating with an aqueous silver nitrate solution for varying times, on growth of the Gram-positive bacterium, S. aureus.
Figure 3:
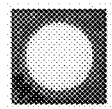
FIG. 3 shows the effect of siloxane-based coatings, both with and without quaternary ammonium groups after treatment of the coating with an aqueous silver nitrate solution for varying times, on growth of the Gram-negative bacterium, E. coli.
Figure 3:
Figure 4:
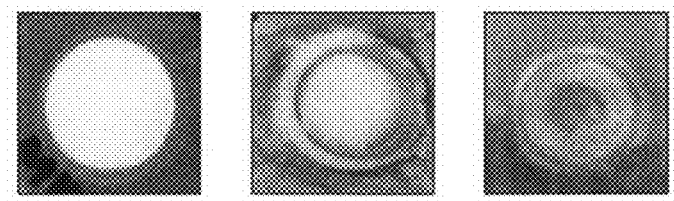
FIG. 4 shows examples of agar plates which either exhibit inhibition of bacterial growth at the surface and a zone of inhibition (left; "+, +"); inhibition of bacterial growth at the surface but no zone of inhibition (center; "+, −"); or no inhibition of bacterial growth at the surface or the formation of a zone of inhibition (right; "−, −") after being inoculated (via swab) with a designated microbial culture and then subsequently placed in contact with the surface of an aluminum disk having a coating including either an example of the present polymeric material or with a control.

Silanol-terminated polydimethylsiloxane (PDMS), QAS-functional trimethoxysilanes, and methyltriacetoxysilane were reacted together in the presence of TBAF catalyst solution to form a crosslinked network where the QAS was tethered to the PDMS matrix. Curing and QAS tethering occurred by a mixture of condensation reactions involving Si—OH, acetoxysilane, and methoxysilane groups. Cured coatings were immersed in 5% aqueous silver nitrate solution for 1, 4, and 6 days. After immersion, the coatings were evaluated against *S. aureus* and *E. coli* and the results were compared with crosslinked-PDMS coatings without any tethered QAS. The results of *S. aureus* and *E. coli* are shown in FIG. 2 and FIG. 3 respectively.

Since PDMS coatings with tethered QAS were effective against both organisms, a follow-up experiment was carried out to determine the effect of immersion time of the coatings in aqueous silver nitrate solution on antimicrobial activity. Coatings were immersed in 5%, 10%, and 20% aqueous silver nitrate solution for 2 h, 6 h, and 24 h and were evaluated against *E. coli* and *S. aureus*. For control coatings (no QAS), only 24 h immersion time was used. The results for *E. coli* and *S. aureus* are shown in Tables 1 and 2 respectively.

TABLE 1

Coatings Exposed to AgNO₃ Solution

| | | S-15 | | S-27 | | S-35 | |
|---|---|---|---|---|---|---|---|
| | | With QAS | Without QAS | With QAS | Without QAS | With QAS | Without QAS |
| 0 | | − | | − | | − | |
| 2 hr | 5% | − | | + | | + | |
| | 10% | − | | + | | + | |
| | 20% | − | | + | | + | |
| 6 hr | 5% | − | | + | | + | |
| | 10% | − | | + | | + | |
| | 20% | − | | + | | + | |
| 24 hr | 5% | − | − | + | − | + | − |
| | 10% | + | − | + | − | + | − |
| | 20% | + | − | + | − | + | + |

+ − Zone of inhibition
− − No zone of inhibition

TABLE 2

Coatings Exposed to AgNO₃ Solution

| | | S-15 | | S-27 | | S-35 | |
|---|---|---|---|---|---|---|---|
| | | With QAS | Without QAS | With QAS | Without QAS | With QAS | Without QAS |
| 0 | | − | | − | | − | |
| 2 hr | 5% | − | | + | | + | |
| | 10% | − | | + | | + | |
| | 20% | − | | + | | + | |
| 6 hr | 5% | + | | + | | + | |
| | 10% | + | | + | | + | |
| | 20% | + | | + | | + | |
| 24 hr | 5% | + | − | + | − | + | − |
| | 10% | + | − | + | − | + | − |
| | 20% | + | − | + | − | + | + |

+ − Zone of inhibition
− − No zone of inhibition

The results indicate that high molecular weight PDMS (18K and 49K) with tethered QAS were more effective in releasing silver ions. The time of immersion could be as low as 2 h in 5% aqueous silver nitrate. Coatings without QAS were not effective in releasing silver ions under identical conditions.

High molecular weight PDMS with tethered QAS could act as a matrix for releasable silver ions and were found to be effective against *E. coli* and *S. aureus*. Under the explored design space, minimum time of immersion of PDMS-QAS coatings were 2 h in 5% aqueous silver nitrate to release silver ions.

Example 4

PDMS-QAS Coatings with Releasable Silver Ions/Silver Nanoparticles

Materials. 18,000 g/mole silanol-terminated polydimethylsiloxane (PDMS 18K, S-27), octadecyldimethyl(3-trimethoxysilylpropyl) ammoniumchloride (C18-QAS, SIO 6620), n-octadecyltrimethoxysilane (C18-Xlink, SIO6645), and methyltriacetoxysilane (SIM6519, MeAc) were purchased from Gelest. 1.0 M tetrabutylammoniumfluoride (TBAF) in tetrahydrofuran and silver nitrate were obtained from Aldrich. Toluene was obtained from VWR. 4-Methyl-2-pentanone was purchased from Alfa Aesar. Silver nanoparticles GA-AgNP (0.45 mg/ml of Ag conc.) and S1-AgNP (0.45 mg/ml of Ag conc.) were obtained from University of Missouri. Aqueous solution of silver nitrate and 50 mmolar TBAF in 4-methyl-2-pentanone (Cat sol) were prepared while all other reagents were used as received.

Coating preparation: Coating with tethered QAS was prepared by mixing 3.5 g of PDMS, 0.579 g of C-18 QAS, 0.525 g of MeAc, and 0.525 g of cat sol in a 20 ml vial. After through mixing, depositions were made over primed aluminum discs. Coatings were cured for 24 h at room temperature, followed by an additional 24 h in an oven at 50° C. Control coating, i.e. coating without tethered QAS was prepared by mixing 3.5 g of PDMS, 0.26 g of C18-Xlink, 0.525 g of MeAc, and 0.525 g of cat sol in a 20 ml vial. After through mixing, depositions were made over primed aluminum discs. Coatings were cured for 24 h at room temperature, followed by an additional 24 h in an oven at 50° C. Cured coatings were immersed in aqueous silver nitrate solution of different concentrations for different time period. After immersion, coatings were rinsed with water and dried at room temperature for 24 h.

Results and Discussion

Silanol-terminated polydimethylsiloxane (PDMS), QAS-functional trimethoxysilanes, and methyltriacetoxysilane were reacted together in the presence of TBAF catalyst solution to form a crosslinked network where the QAS was tethered to the PDMS matrix. Curing and QAS tethering occurred by a mixture of condensation reactions involving Si—OH, acetoxysilane, and methoxysilane groups. Cured coatings were immersed in the following solutions for 2 and 6 hr. The solutions are:

Silver nanoparticle GA-AgNP (0.45 mg/ml of Ag conc.)
Silver nanoparticle S1-AgNP (0.45 mg/ml of Ag conc.)
Aqueous silver nitrate solution AgNO3-L (0.45 mg/ml of Ag ion conc.)
5 wt % aqueous silver nitrate solution AgNO3-H (33.4 mg/ml of Ag ion conc.)

After immersion, the coatings were evaluated against *E. coli* and the results were compared with crosslinked-PDMS coatings without any tethered QAS. The results for *E. coli* are shown in Table 3.

TABLE 3

Coatings with Ag Nanoparticles or AgNO₃ Solution

| | | S-27 | |
|---|---|---|---|
| | | With QAS | Without QAS |
| 0 | | − | − |
| 2 hr | GA AgNP | + | − |
| | S1 AgNP | + | − |
| | AgNO₃-1 | + | − |
| | AgNO₃-2 | + | − |
| 6 hr | GA AgNP | + | − |
| | S1 AgNP | + | − |
| | AgNO₃ - L | + | − |
| | AgNO₃ - H | + | − |

+ - Zone of inhibition
− - No zone of inhibition

High molecular weight PDMS with tethered QAS could act as a matrix for releasable silver nanoparticles and silver ions and were found to be effective against *E. coli*. Under the explored design space, immersion of PDMS-QAS coatings for two hours were sufficient to release silver nanoparticles (or soluble silver species derived therefrom) or silver ions (e.g., in the form of silver nitrate salt).

Example 5

For Example 5, 3.5 g of PDMS-2K, 0.58 g of C-18 QAS, 0.53 g of MeAc, and 0.53 g of cat sol were combined in a 20 ml glass vial. After thoroughly mixing using a vortex mixer, depositions were made by dispensing approximately 200 μL of coating solution over 15 mm aluminum discs primed with Intergard 264 epoxy. Coatings were allowed to cure for 24 h at room temperature, followed by an additional 24 h in an oven at 50° C. For Reference 5, 3.5 g of PDMS-2K, 0.26 g of C18-Xlink, 0.53 g of MeAc, and 0.53 g of cat sol were used to prepare the coating solution. Coating deposition and curing were done using the same procedure described for Example 5.

Coated discs of Example 5 and Reference 5 were immersed a 5 weight percent aqueous solution of silver nitrate for different periods of time. After immersion, coatings were rinsed with water and dried at room temperature for 24 h before antimicrobial testing.

Antimicrobial testing towards *Escherichia coli* and *Staphylococcus aureus* was done using an agar plating method. Stocks of *Escherichia coli* ATCC 12435 and *Staphylococcus aureus* ATCC 25923 and were maintained weekly at 4° C. on LBA, TSB and SDA, respectively. Broth cultures of *E. coli* (LBB), *S. aureus* (TSB), and *C. albicans* (YNB) were prepared by inoculating one colony into 10 ml of broth and incubating at 37° C. with shaking. Overnight cultures were pelleted via centrifugation (10 min at 4500 rpm), washed twice in PBS, and resuspended to a final cell density of ~$10^8$ cells·$ml^{-1}$. A sterile swab was used to inoculate a lawn of each microorganism on their corresponding agar plates. The coated aluminum discs were then placed on the agar plates with the coated side in direct contact with the agar surface. The plates were inverted and incubated for 24 hours at 37° C. Inhibition of microbial growth around and/or directly on the coating surfaces was evaluated visually from digital images taken after 24 hours of incubation. A biological activity indicator dye, triphenyltetrazolium chloride, was added to the agar medium (70 mg/l *E. coli* and 15 mg/l *S. aureus*) to aid in the visualization of microbial growth (i.e., red color).

The results displayed in Table 4 show that immersion of Example 5 in aqueous silver nitrate for a minimum of 24 hours enabled antimicrobial activity toward both *E. coli* and *S. aureus* while no antimicrobial activity was observed for Reference 5 even after being exposed to 5 weight percent aqueous silver nitrate for 144 hours.

TABLE 4

Antimicrobial activity for Example 5 and Reference 5 after immersion in aqueous silver nitrate solutions for various durations.

| Immersion Time in AgNO₃ (hours) | AgNO₃ conc. (wt. %) | Reference 5 challenged with *E. coli* | Example 5 challenged with *E. coli* | Reference 5 challenged with *S. aureus* | Example 5 challenged with *S. aureus* |
|---|---|---|---|---|---|
| 0 | — | −, − | −, − | −, − | −, − |
| 2 | 5 | −, − | +, − | −, − | +, − |
| 6 | 5 | −, − | +, − | −, − | +, + |
| 24 | 5 | −, − | +, + | −, − | +, + |
| 96 | 5 | −, − | +, + | −, − | +, + |
| 144 | 5 | −, − | +, + | −, − | +, + |
| 2 | 10 | −, − | +, − | −, − | +, − |
| 6 | 10 | −, − | +, − | −, − | +, + |
| 24 | 10 | −, − | +, + | −, − | +, + |
| 2 | 20 | −, − | +, − | −, − | +, − |
| 6 | 20 | −, − | +, − | −, − | +, + |
| 24 | 20 | −, − | +, + | −, − | +, + |

"+, +" indicates inhibition of bacterial growth at the surface and a zone of inhibition; "+, −" indicates inhibition of bacterial growth at the surface but no zone of inhibition; "−, −" indicates no inhibition of bacterial growth at the surface or the formation of a zone of inhibition.

Example 6

The composition of Example 6 is the same as Example 5 with the exception that PDMS-18K was used in place of PDMS-2K. The composition of Reference 6 is the same as Reference 5 with the exception that PDMS-18K was used in place of PDMS-2K. The material preparation and testing procedures used for Example 6 and Reference 6 are the same as used for Example 5 and Reference 5, respectively. The results obtained are shown in Table 5.

The results displayed in Table 5 show that immersing Example 6 in 5 weight percent aqueous silver nitrate for 2 hours provided antimicrobial activity toward both *E. coli* and *S. aureus* while no activity was observed for Reference 6 even after immersing in 20 weight percent aqueous silver nitrate for 24 hours. Comparing the results obtained for Example 6 to the results obtained for Example 5, it can be seen that Example 6 required less immersion time to obtain antimicrobial activity than Example 5.

TABLE 5

Antimicrobial activity for Example 6 and Reference 6 after immersion in aqueous silver nitrate solutions for various durations.

| Immersion Time in AgNO₃ (hours) | AgNO₃ concentration (wt. %) | Ref. 6 challenged with *E. coli* | Example 6 challenged with *E. coli* | Ref. 6 challenged with *S. aureus* | Example 6 challenged with *S. aureus* |
|---|---|---|---|---|---|
| 0 | — | −, − | +, − | −, − | +, − |
| 2 | 5 | −, − | +, + | −, − | +, + |
| 6 | 5 | −, − | +, + | −, − | +, + |
| 24 | 5 | −, − | +, + | −, − | +, + |
| 96 | 5 | −, − | +, + | −, − | +, + |
| 144 | 5 | −, − | +, + | −, − | +, + |
| 2 | 10 | −, − | +, + | −, − | +, + |
| 6 | 10 | −, − | +, + | −, − | +, + |
| 24 | 10 | −, − | +, + | −, − | +, + |
| 2 | 20 | −, − | +, + | −, − | +, + |

TABLE 5-continued

Antimicrobial activity for Example 6 and Reference 6 after immersion
in aqueous silver nitrate solutions for various durations.

| Immersion Time in AgNO$_3$ (hours) | AgNO$_3$ concentration (wt. %) | Ref. 6 challenged with E. coli | Example 6 challenged with E. coli | Ref. 6 challenged with S. aureus | Example 6 challenged with S. aureus |
|---|---|---|---|---|---|
| 6 | 20 | −, − | +, + | −, − | +, + |
| 24 | 20 | −, − | +, + | −, − | +, + |

"+, +" indicates inhibition of bacterial growth at the surface and a zone of inhibition; "+, −" indicates inhibition of bacterial growth at the surface but no zone of inhibition; "−, −" indicates no inhibition of bacterial growth at the surface or the formation of a zone of inhibition.

Example 7

The composition of Example 7 was the same as Example 6 and the composition of Reference 7 was the same as Reference 6. Coating solution preparation and coating solution deposition onto aluminum discs for Example 7 and Reference 7 were that same as used for Example 5 and Reference 5, respectively. The coated discs were immersed in a silver nitrate solution (45 mg Ag/ml of solution) for 0.25 or 2 hours, rinsed, allowed to dry at room temperature for 24 hours. The coated discs were then glued to the bottoms of 24-well polystyrene array plates using DowCorning® RTV sealant 734. Coating specimens were arranged in the 24-well array plate (6 columns and 4 rows) such that a given coating composition occupied an entire column of the 24 well array plate (4 replicate coatings per array plate). These array plates were used to determine bacterial biofilm retention.

The procedure used for the biofilm retention assay is as follows: *Escherichia coli* ATCC 12435 and *Staphylococcus aureus* ATCC 25923 were received as lyophilized powders and revived in LBB and TSB, respectively. Revived cultures were subcultured twice and stored in frozen 1.0-ml aliquots of LBB or TSB containing 30% glycerol in a −80° C. freezer. Stocks of *E. coli* and *S. aureus* were maintained weekly at 4° C. on LBA and TSA, respectively. Broth cultures of each microorganism were prepared by inoculating one colony from an agar plate into 10 ml of broth and incubating at 37° C. with shaking. Overnight cultures were pelleted via centrifugation (10 min at 4500 rpm), washed twice in 1×PBS, and resuspended to a final cell density of ~$10^8$ cells·ml$^{-1}$ in the appropriate biofilm growth medium. In this regard, TSB+2.5% dextrose was utilized to facilitate *S. aureus* biofilm growth and M63 minimal medium (1×) supplemented with dextrose (2.0 g/l) and MgSO$_4$ (0.125 g/l) was utilized for *E. coli* biofilm growth. 1.0 ml of each microorganism suspension in BGM was added to rows 2-4 for each coating plate. Row 1 received 1.0 ml of sterile BGM only (no microorganism) and served as an assay control. To promote optimal biofilm growth on the coating surfaces, coating plates were incubated statically at 37° C. for 24 hrs.

After incubation, the coating plates were rinsed three times in deionized water to remove any planktonic growth or loosely attached cells and allowed to air dry at ambient laboratory conditions. 0.5 ml of crystal violet (CV) was then added to each well for 15 minutes to stain the biofilm retained on the coating surfaces after rinsing. The plates were rinsed three times with deionized water to remove excess CV, inverted and tapped firmly against a paper towel, air dried at ambient laboratory conditions, and imaged with a digital camera. 0.5 ml of 33% glacial acetic acid was then added to each well for 15 minutes to solublize the CV dye. A custom extraction template was applied to each plate prior to the addition of acetic acid to prevent biofilms retained on the well walls from being included in the CV analysis. 0.15 ml of the resulting eluates were transferred to a 96-well plate and measured for absorbance at 600 nm using a Saphire multi-well plate reader (Tecan Group Ltd., Raleigh, N.C.). The amount of biofilm retained on the coating surfaces was directly proportional to the absorbance measurements.

An additional set of coating plates was prepared and inoculated as described above and used for the rapid evaluation of bacterial viability on the coating surfaces. Immediately after rinsing/removing the planktonic growth and loosely attached cells, 0.25 ml of BacTiter-Glo™ luminescence reagent and 0.25 ml of 1×PBS was added to each well and allowed to incubate for 5 minutes on an orbital shaker (150 rpm) at ambient laboratory conditions. Aliquots (0.15 ml) were transferred to an opaque, white walled 96-well plate and measured for luminescence (at an appropriate gain) using the Saphire multi-well plate reader. The luminescence intensity values obtained were directly proportional to the amount of viable bacterial cells residing in the biofilm and/or on the coating surfaces.

Figure 5:
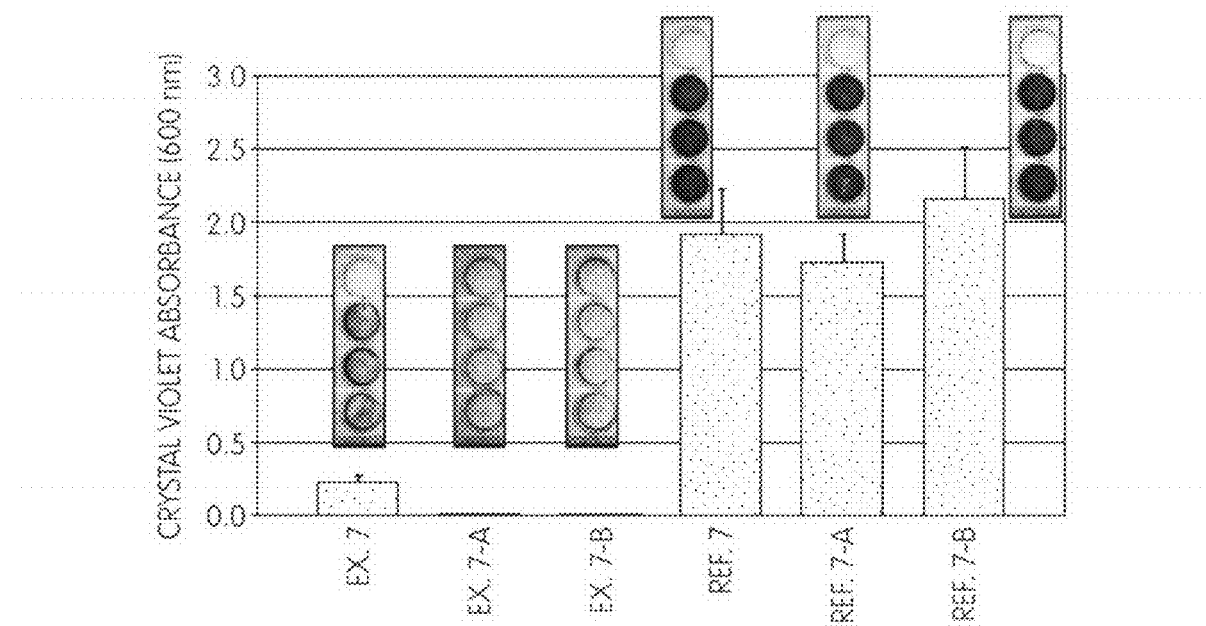
FIG. 5 depicts a graph which shows results obtained from the E. coli biofilm retention assay. The samples labeled "Ex. 7" and "Ref 7" were not exposed to a silver solution. The samples labeled "Ex. 7-A" and "Ref 7-A" were exposed to a silver nitrate solution for 0.25 hr. The samples labeled "Ex. 7-B" and "Ref 7-B" were exposed to a silver nitrate solution for 2 hr. The images in the figure correspond to columns in the array plates. The top row of the column was not inoculated with E. coli, but was subjected to staining with crystal violet. This well is used to ensure that crystal violet uptake is purely due to biofilm formation and not to binding by the coating.
Figure 6:
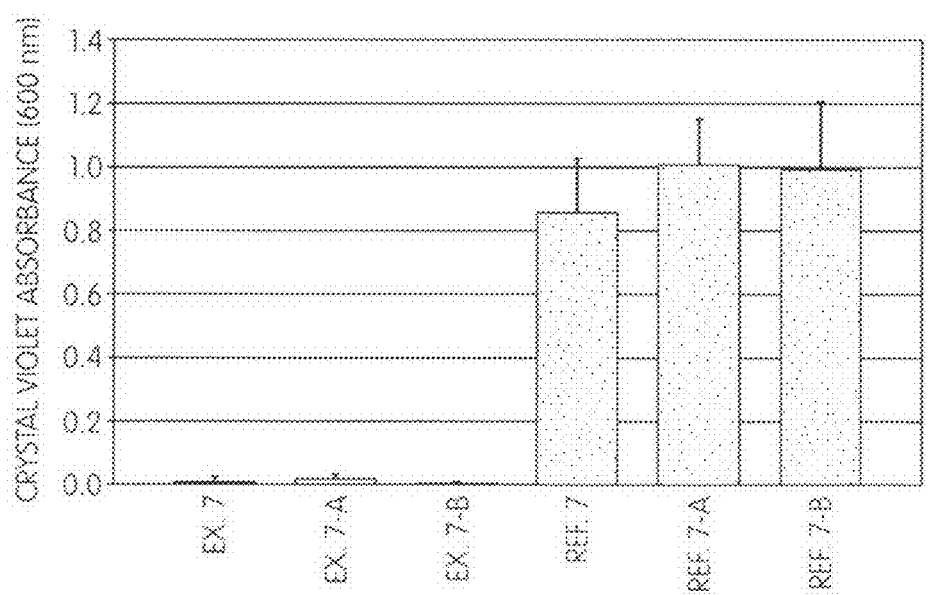
FIG. 6 depicts a graph which shows results obtained from the S. aureus biofilm retention assay with the samples prepared as described in Example 7.
Figure 7:
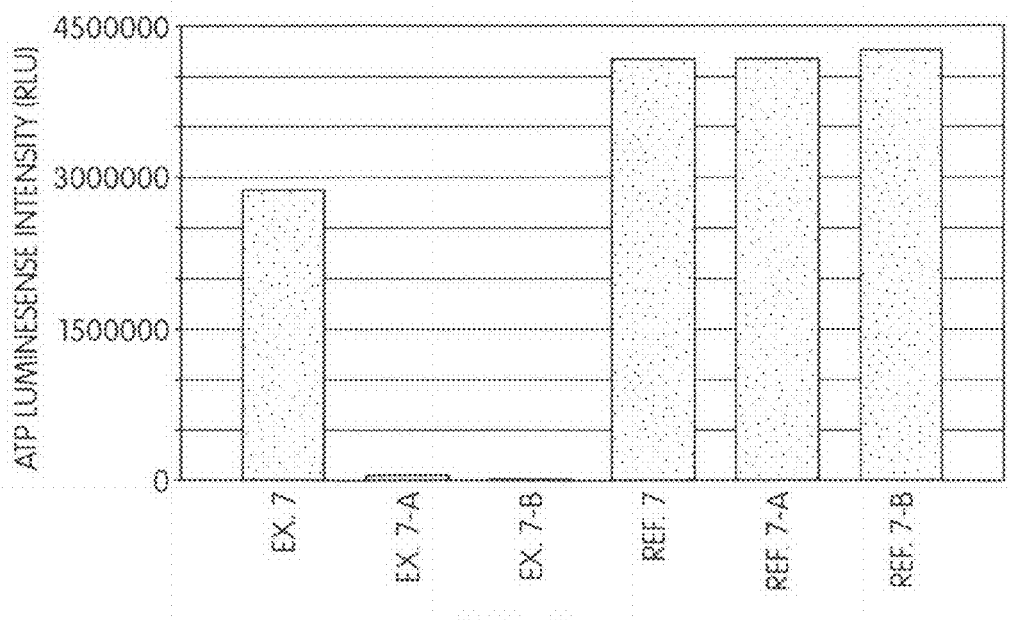
FIG. 7 depicts a graph which shows results obtained from the E. coli biofilm viability assay with the samples prepared as described in Example 7.
Figure 8:
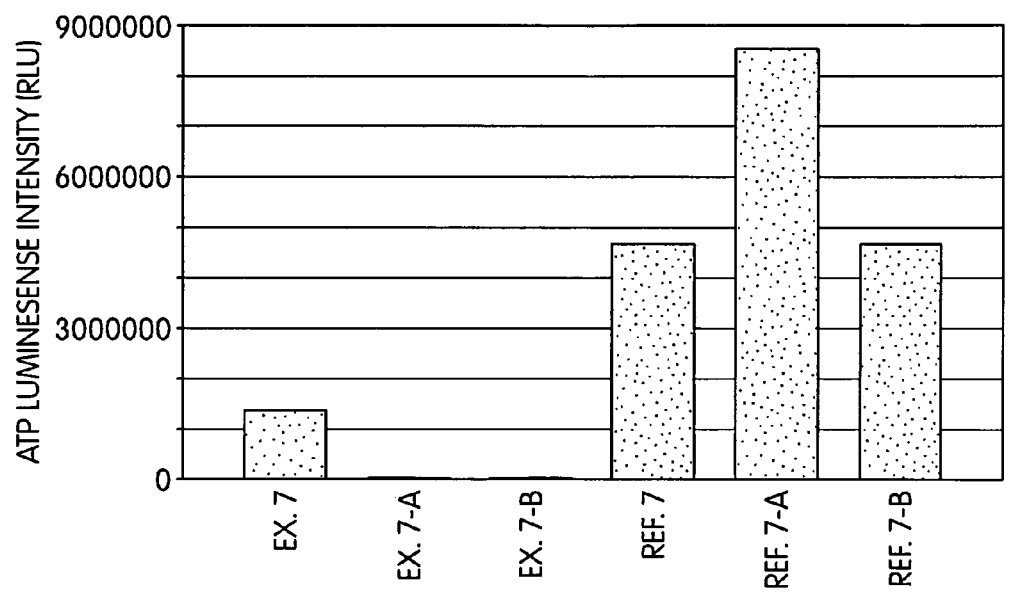
FIG. 8 depicts a graph which shows results obtained from the S. aureus biofilm viability assay with the samples prepared as described in Example 7.

The results obtained for *E. coli* and *S. aureus* biofilm retention are shown in FIGS. 5 and 6, respectively. FIGS. 7 and 8 show the viability results for *E. coli* and *S. aureus*, respectively. FIGS. 5 and 6 show no significant biofilm was retained on Example 7 treated with a silver nitrate solution while a heavy biofilm was retained on Reference 7 treated with a silver nitrate solution. In addition, the untreated (no immersion in the silver nitrate solution) Example 7 material showed excellent antimicrobial activity illustrating the inherent antimicrobial activity of this coating.

FIGS. 7 and 8 show that Example 7 treated with a silver nitrate solution shows essential no viable bacterial cells on the coating surface while high bacterial cell viability was obtained for Reference 7 treated with a silver nitrate solution. In addition, the untreated (no immersion in the silver nitrate solution) Example 7 material showed reduced bacterial cell viability compared to Reference 7 and the silver nitrate treated variations of Reference 7, but higher viability than the silver nitrate treated variations of Example 7.

Example 8

The composition of Example 8 is the same as Example 5 with the exception that PDMS-49K was used in place of PDMS-2K. The composition of Reference 8 is the same as Reference 8 with the exception that PDMS-49K was used in place of PDMS-2K. The material preparation and testing procedures used for Example 8 and Reference 8 were the same as used for Example 5 and Reference 5, respectively. The results obtained are shown in Table 6.

The results displayed in Table 6 show that immersing Example 8 in 5 weight percent aqueous silver nitrate for 2 hours provided antimicrobial activity toward both *E. coli* and *S. aureus* while Reference 8 required an immersion time of 24 hours and a silver nitrate concentration of 20 weight percent to obtain antimicrobial activity. Comparing the results obtained for Example 8 to the results obtained for Example 5, it can be seen that Example 8 required less immersion time to obtain antimicrobial activity than Example 5.

TABLE 6

Antimicrobial activity for Example 8 and Reference 8 after immersion in aqueous silver nitrate solutions for various durations.

| Immersion Time in AgNO$_3$ (hours) | AgNO$_3$ conc. (wt. %) | Ref. 8 challenged with E. coli | Example 8 challenged with E. coli | Ref. 8 challenged with S. aureus | Example 8 challenged with S. aureus |
|---|---|---|---|---|---|
| 0 | — | −, − | −, − | −, − | +, − |
| 2 | 5 | −, − | +, + | −, − | +, + |
| 6 | 5 | −, − | +, + | −, − | +, + |
| 24 | 5 | −, − | +, + | −, − | +, + |
| 96 | 5 | −, − | +, + | −, − | +, + |
| 144 | 5 | −, − | +, + | −, − | +, + |
| 2 | 10 | −, − | +, + | −, − | +, + |
| 6 | 10 | −, − | +, + | −, − | +, + |
| 24 | 10 | −, − | +, + | −, − | +, + |
| 2 | 20 | −, − | +, + | −, − | +, + |
| 6 | 20 | −, − | +, + | −, − | +, + |
| 24 | 20 | +, + | +, + | +, + | +, + |

"+, +" indicates inhibition of bacterial growth at the surface and a zone of inhibition; "+, −" indicates inhibition of bacterial growth at the surface but no zone of inhibition; "−, −" indicates no inhibition of bacterial growth at the surface or the formation of a zone of inhibition.

Example 9

The composition of Example 9 was the same as Example 6 and the composition of Reference 9 was the same as Reference 6. The material preparation and testing procedures used for Example 9 and Reference 9 were the same as used for Example 5 and Reference 5, respectively. In addition to immersion in aqueous silver nitrate, this example involves immersion in two different colloidal dispersions of silver nanoparticles (GA-AgNP and S1-AgNP). The results obtained are shown in Table 7.

The results displayed in Table 7 show that immersing Example 9 in a colloidal dispersion of silver nanoparticles for as little as 15 minutes provides antimicrobial activity toward E. coli while immersion of Reference 9 in the same colloidal dispersion of silver nanoparticles results in no antimicrobial activity even when the immersion time is increased to 6 hours. In addition, the results show that antimicrobial activity for Example 9 can be obtained by immersion for just 15 minutes in a very dilute solution of silver nitrate (0.067 weight percent).

TABLE 7

Antimicrobial activity for Example 9 and Reference 9 after immersion in silver nanoparticle/aqueous silver nitrate solutions for various durations.

| Immersion Time (hours) | AgNO$_3$ conc. (mg Ag/ml of solution) | GA-AgNP conc. (mg Ag/ml of solution) | S1-AgNP conc. (mg Ag/ml of solution) | Ref. 9 challenged with E. coli | Example 9 challenged with E. coli |
|---|---|---|---|---|---|
| 0 | — | — | — | −, − | +, − |
| 0.25 | 0.45 | — | — | −, − | +, + |
| 1 | 0.45 | — | — | −, − | +, + |
| 2 | 0.45 | — | — | −, − | +, + |
| 6 | 0.45 | — | — | −, − | +, + |
| 2 | 33.4 | — | — | −, − | +, + |
| 6 | 33.4 | — | — | −, − | +, + |
| 0.25 | — | 0.45 | — | −, − | +, + |
| 1 | — | 0.45 | — | −, − | +, + |
| 2 | — | 0.45 | — | −, − | +, + |
| 6 | — | 0.45 | — | −, − | +, + |
| 2 | — | — | 0.45 | −, − | +, + |
| 6 | — | — | 0.45 | −, − | +, + |

"+, +" indicates inhibition of bacterial growth at the surface and a zone of inhibition; "+, −" indicates inhibition of bacterial growth at the surface but no zone of inhibition; "−, −" indicates no inhibition of bacterial growth at the surface or the formation of a zone of inhibition.

Example 10

The composition of Example 10 was the same as Example 6 and the composition of Reference 10 was the same as Reference 6. The material preparation procedure used for Example 10 and Reference 10 were the same as those used for Example 6 and Reference 6, respectively. The samples were immersed in various aqueous silver-containing solutions at room temperature. After treating with samples with the immersion process, the samples were placed in PBS for 15 days and subsequently rinsed before determining antimicrobial activity toward E. coli. The purpose of immersing the silver treated samples in PBS prior to antimicrobial testing was to characterize the longer-term silver release properties of the materials. The results obtained are shown in Table 8 below.

The results displayed in Table 8 show antimicrobial activity for Example 10 even after being immersed in PBS for 15 days. Reference 10 showed no antimicrobial activity. The results also show that maintenance of antimicrobial activity after PBS exposure is enhanced with the use of silver nanoparticles.

TABLE 8

Antimicrobial activity for Example 10 and Reference 10 after immersion in silver nanoparticle/aqueous silver nitrate solutions for various durations followed by 15 days of preconditioning in PBS.

| Immersion Time (hours) | AgNO$_3$ conc. (mg Ag/ml of solution) | GA-AgNP conc. (mg Ag/ml of solution) | Reference 10 challenged with E. coli | Example 10 challenged with E. coli |
|---|---|---|---|---|
| 0 | — | — | −, − | −, − |
| 0.25 | 0.45 | — | −, − | −, − |
| 1 | 0.45 | — | −, − | −, − |
| 2 | 0.45 | — | −, − | −, − |
| 0.25 | 33.4 | — | −, − | +, + |
| 1 | 33.4 | — | −, − | +, + |
| 2 | 33.4 | — | −, − | +, + |
| 0.25 | — | 0.45 | −, − | +, − |
| 1 | — | 0.45 | −, − | +, − |
| 2 | — | 0.45 | −, − | +, − |

"+, +" indicates inhibition of bacterial growth at the surface and a zone of inhibition; "+, −" indicates inhibition of bacterial growth at the surface but no zone of inhibition; "−, −" indicates no inhibition of bacterial growth at the surface or the formation of a zone of inhibition.

The weight percent of silver in coatings after different treatments with silver-containing solutions was determined using Atomic Absorption Spectroscopy (Galbraith Laboratories). The results obtained are shown in Table 9. Overall, Example 10 takes up much more silver than Reference 10.

TABLE 9

Silver content of Example 10 and Reference 10 after immersion in a 0.45 mg Ag/ml solution of GA-AgNP for different periods of time.

| Immersion Time (hours) | AgNO$_3$ concentration (mg Ag/ml of solution) | GA-AgNP concentration (mg Ag/ml of solution) | Reference 10 (wt. %) | Example 10 (wt. %) |
|---|---|---|---|---|
| 0.25 | 0.45 | — | $0.66 \times 10^{-2}$ | $0.98 \times 10^{-2}$ |
| 2 | 0.45 | — | $0.96 \times 10^{-2}$ | $8.85 \times 10^{-2}$ |
| 0.25 | — | 0.45 | $0.66 \times 10^{-2}$ | $1.28 \times 10^{-2}$ |
| 2 | — | 0.45 | $0.94 \times 10^{-2}$ | $2.68 \times 10^{-2}$ |

Silver content was determined using Atomic Absorption Spectroscopy.

Illustrative Embodiments

The following exemplary embodiments are presented to illustrate the present polymer-based composite materials, coatings and methods to assist one of ordinary skill in making and using the same. These illustrative embodiments are not intended in any way to otherwise limit the scope of the invention described herein.

In one embodiment, a substrate (A) may have a coating on its surface, and the coating may comprise a polymeric material which includes tetraalkyl-substituted quaternary amino functionalized cross-linked polysiloxane and a plurality of metal species, such as silver species. The coating suitably includes an antimicrobially effective amount of metal species, e.g., silver species, distributed within the polymeric material.

In another embodiment, a coated substrate (B) can include a plurality of metal species, such as silver species, and quaternary amino functionalized cross-linked polysiloxane, which may be prepared by reacting a mixture which includes alkoxysilyl functionalized quaternary amine and silanol terminated polysiloxane. In the coated substrate of embodiment B, the reaction mixture may further comprise alkyltriacyloxysilane. In the coated substrate of embodiment B, the mixture may further comprise a tetra-functional acyloxysilane and/or alkoxysilane. In the coated substrate of embodiment B, the mixture may further comprise a trifunctional silane in which the reactive functionality is selected from the group that may consist of alkoxysilane, acyloxysilane, silazane, halosilane, and ketoxime-based silane. In the coated substrate of embodiment B, the mixture may further comprise a tetra-functional silane in which the reactive functionality may be selected from the group consisting of alkoxysilane, acyloxysilane, silazane, halosilane, and ketoxime-based silane.

In other embodiments of the present compositions and materials, a coated substrate (C) may include (i) quaternary amino functionalized cross-linked polysiloxane that may be prepared by reacting a mixture which may include silyl functionalized quaternary amine and polysiloxane with reactive terminal groups and (ii) a plurality of metal species, such as silver species, distributed within the polymeric material. In the coated substrate of embodiment C, the silyl functionalized quaternary amine may includes a reactive functionality selected from the group that may consist of alkoxysilane, acyloxysilane, silazane, halosilane, and ketoxime-based silane. In the coated substrate of embodiment C, the polysiloxane with reactive terminal groups may include a reactive functionality selected from the group that may consist of silanol, alkoxysilane, acyloxysilane, silazane, halosilane, and ketoxime-based silane.

In another embodiment, a coated substrate (D) can include (i) quaternary amino functionalized cross-linked polysiloxane that may be prepared by reacting a mixture which may include alkoxysilyl functionalized quaternary amine, silanol terminated polysiloxane, and alkyltriacyloxysilane; and (ii) a plurality of metal species, such as silver species, distributed within the polymeric material.

In the coated substrate of embodiment D, the silanol terminated polysiloxane may be a silanol terminated polydialkylsiloxane (e.g., a silanol terminated polydimethylsiloxane), and may preferably have a molecular weight of about 1,000 to about 100,000, desirably have a molecular weight of about 10,000 to about 75,000, and more desirably have a molecular weight of about 15,000 to about 50,000.

In another embodiment, the coated substrate (E) can include (i) a plurality of metal species, such as silver species, distributed within the polymeric material; and (ii) alkoxysilyl functionalized quaternary amine

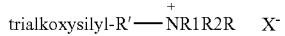

where R1 and R2 may be lower alkyl groups, R may be an alkyl group having 5 to 25 carbon atoms, R' may be a linker group, such as an alkylene and/or benzylidene group, and X may be a halide. In the coated substrate of embodiment E, R' may be ethylene and/or propylene, R1 and R2 may be methyl, benzyl and/or ethyl, and X may be a halide, such as chloride, iodide and/or bromide. In the coated substrate of embodiment E, R' may be ethylene, propylene and/or benzylidene. In the coated substrate of embodiment E, R1 and R2 may be methyl; and X may be chloride. In the coated substrate of embodiment E, R may be an n-alkyl group having 5 to 25 carbon atoms. In the coated substrate of embodiment E, R may be an n-alkyl group having at least 10 carbon atoms. In the coated substrate of embodiment E, R may be an n-alkyl group having no more than 20 carbon atoms. In the coated substrate of embodiment E, R may be an n-alkyl group having 12 to 20 carbon atoms. In the coated substrate of embodiment E, R may be an n-alkyl group having 12 to 16 carbon atoms. In the coated substrate of embodiment E, R may be an n-alkyl group having 16 to 20 carbon atoms. In the coated substrate of embodiment E, the alkoxysilyl functionalized quaternary amine may include a trialkoxysilyl group having no more than 6 carbon atoms. In the coated substrate of embodiment E, the alkoxysilyl functionalized quaternary amine may include a trimethoxysilyl group. In the coated substrate of embodiment E, the alkyltriacyloxysilane may be an alkyltriacetoxysilane. In the coated substrate of embodiment E, the alkyltriacyloxysilane may include methyltriacetoxysilane.

In another embodiment, a polymeric material (F) can be prepared by reacting a mixture which may include alkoxysilyl functionalized quaternary amine; silanol terminated polysiloxane; and alkyltriacyloxysilane. This may be combined with (i) a plurality of metal species, such as silver species, such that the metal species are distributed within the polymeric material. In the polymeric material of embodiment F, the mixture may further comprise tetraalkyl ammonium fluoride salt and/or tetraalkyl phosphonium fluoride salt. The polymeric material of embodiment F may be formed from a mixture comprising about 0.001 to 0.05 moles of the alkoxysilyl functionalized quaternary amine per 100 gm of the silanol terminated polysiloxane. The polymeric material of embodiment F may be formed from a mixture comprising about 0.005 to 0.03 moles trialkoxysilyl functionalized quaternary amine per 100 gm of silanol terminated polydialkylsiloxane. The polymeric material of embodiment F may be formed from a mixture comprising about 0.015 to 0.025 moles trialkoxysilyl functionalized quaternary amine per 100 gm of silanol terminated polydimethylsiloxane. In the polymeric material of embodiment F, the trialkoxysilyl functionalized quaternary amine may include an N—C18-alkyl-N,N-dimethylamino group. In the polymeric material of embodiment F, the trialkoxysilyl functionalized quaternary amine may include an N—C14-alkyl-N,N-dimethylamino group. In the polymeric material of embodiment F, the trialkoxysilyl functionalized quaternary amine may include an N—(C16-C20)-n-alkyl-N,N-dimethylamino group. In the polymeric material of embodiment F, the trialkoxysilyl functionalized quaternary amine may include an N—(C12-C16)-n-alkyl-N,N-dimethylamino group.

In another embodiment, a polymer-based composite comprises (i) a plurality of metal species, such as silver species, distributed within the polymeric material; and (ii) a polymeric material (G) prepared by reacting a mixture which may include trialkoxysilyl functionalized quaternary amine, silanol terminated polydialkylsiloxane, and alkyltriacyloxysilane.

In another embodiment, a polymeric material (H) may be prepared by reacting a mixture which may include trimethoxysilyl functionalized quaternary amine, silanol terminated polydialkylsiloxane, and methyltriacetoxysilane. The polymeric material (H) is combined with a plurality of metal species, such as silver species, such that the metal species are distributed within the polymeric material. The metal species may be distributed throughout the polymeric material. In certain embodiments, e.g., when the metal species are introduced into the polymeric material by contacting a solution containing the metal species with a coating formed from the polymeric material, the metal species may predominantly be distributed within the polymeric material in an outer portion of the coating.

In another embodiment, an antimicrobial polymer coating (I) can comprise (i) quaternary amino functionalized cross-linked polysiloxane and/or salts thereof; and (ii) a plurality of metal species, such as silver species, distributed within the polymeric material. In the polymer coating of embodiment I, the quaternary amino functionalized cross-linked polysiloxane may be prepared by reacting a mixture which may include alkoxysilyl functionalized quaternary amine, silanol terminated polysiloxane, and alkyltriacyloxysilane. In the polymer coating of embodiment I, the quaternary amino functionalized cross-linked polysiloxane may include silyl functionalized quaternary amino moieties, which may include an N—(C10-C25)-n-alkyl-N,N-dimethylamino group. In the polymer coating of embodiment I, the quaternary amino functionalized cross-linked polysiloxane may include silyl functionalized quaternary amino moieties, which may include an N—(C12-C16)-n-alkyl-N,N-dimethylamino group. In the polymeric material of embodiment I, the mixture may further comprise tetrabutyl ammonium fluoride.

In another embodiment, an amino functionalized cross-linked polysiloxane (J) may be prepared by reacting a mixture, which may include alkoxysilyl functionalized quaternary amine, silanol terminated polysiloxane, and alkyltriacyloxysilane. The functionalized cross-linked polysiloxane (J) may be combined with (ii) a plurality of metal species, such as silver species, distributed within the polymeric material.

Another embodiment provides a method (K) of coating a substrate, which may comprise application of a mixture to the substrate, where the mixture may include alkoxysilyl functionalized quaternary amine, silanol terminated polysiloxane, and alkyltriacyloxysilane, to the substrate. The mixture may also include silver species and/or the initially formed coating may be exposed to a solution which includes silver species in soluble and/or suspended form.

Another embodiment provides a method (L) of inhibiting biofilm growth on a substrate surface, comprising coating the surface with a polymeric material that can include an amino functionalized cross-linked polysiloxane, which may be prepared by reacting a mixture which may include alkoxysilyl functionalized quaternary amine, silanol terminated polysiloxane and alkyltriacyloxysilane. In the method of embodiment L, the alkoxysilyl functionalized quaternary amine may include trialkoxysilyl functionalized quaternary amine that may have an N—(C12-C16)-n-alkyl-N,N-dimethylamino group. In the method of embodiment L, the polymeric material may be formed from a mixture comprising at least about 0.015 moles and, more desirably, at least about 0.02 moles alkoxysilyl functionalized quaternary amine per 100 gm of the silanol terminated polysiloxane. In the method of embodiment L, the polymeric material may be formed from a mixture comprising at least about 0.02 moles alkoxysilyl functionalized quaternary amine per 100 gm of the silanol terminated polysiloxane, and the alkoxysilyl functionalized quaternary amine may include trimethoxysilyl functionalized quaternary amine having an N—(C14)-n-alkyl-N,N-dimethylamino group.

Another embodiment provides a method (M) of inhibiting microbial growth on a substrate surface. The functionalized cross-linked polysiloxane (J) an amino functionalized cross-linked polysiloxane, which may be prepared by reacting a mixture which may include alkoxysilyl functionalized quaternary amine, silanol terminated polysiloxane and alkyltriacyloxysilane. In the method of embodiment M, the alkoxysilyl functionalized quaternary amine can include trialkoxysilyl functionalized quaternary amine having an N—(C16-C20)-n-alkyl-N,N-dimethylamino group. In the method of embodiment M, the polymeric material can be formed from a mixture comprising at least about 0.01 moles alkoxysilyl functionalized quaternary amine per 100 gm of the silanol terminated polysiloxane. In the method of embodiment M, the alkoxysilyl functionalized quaternary amine may include trialkoxysilyl functionalized quaternary amine having an N—C18-alkyl-N,N-dimethylamino group, and the polymeric material may comprise at least about 0.01 moles alkoxysilyl functionalized quaternary amine per 100 gm of the silanol terminated polysiloxane.

In another embodiment, the coated substrate (N) can include the silanol terminated polysiloxane having the formula:

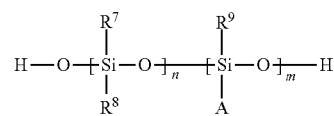

wherein $R^7$, $R^8$, and $R^9$ may be independently alkyl, A may be an alkyl and/or alkoxy group, n may be 0 to 5000, m may be 0 to 2000, and n+m may be at about least 10, and more desirably at least about 25. Commonly, n is at least about 10 and n+m is at least about 20. In the coated substrate of embodiment N, the silanol terminated polysiloxane may have a molecular weight of at least about 500 g/mol. In the coated substrate of embodiment N, the silanol terminated polysiloxane may have a molecular weight of no more than about 50,000 g/mol. In the coated substrate of embodiment N, A may be an alkyl group. In the coated substrate of embodiment N, the silanol terminated polysiloxane may be a silanol terminated polydimethylsiloxane. In the coated substrate of embodiment N, the silanol terminated polysiloxane may be a silanol terminated polyalkylsiloxane.

In another embodiment, a polymeric material (O) may be prepared by reacting a mixture which may include trimethoxysilyl functionalized quaternary amine, silanol terminated polydimethylsiloxane, and methyltriacetoxysilane. The resulting polymeric material may then be combined with a metal species, such a silver species.

In another embodiment, the coated substrate (P) of embodiment O, the trimethoxysilyl functionalized quaternary amine may include

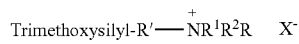

where $R^1$ and $R^2$ may be methyl, R may be an n-alkyl group having 5 to 25 carbon atoms, R' may be a propylene and/or ethylene group, and X may be a halide, such as chloride, iodide and/or bromide. In the coated substrate of embodiment O or P, the silanol terminated polydimethylsiloxane may have a molecular weight of about 1,000 to 50,000.

In one embodiment, the polysiloxane polymer(s) employed to form the present polymeric material includes a cross linked copolymer which is prepared by cross linking a random or block copolymer using a polyamine. The random or block copolymer may have the formula:

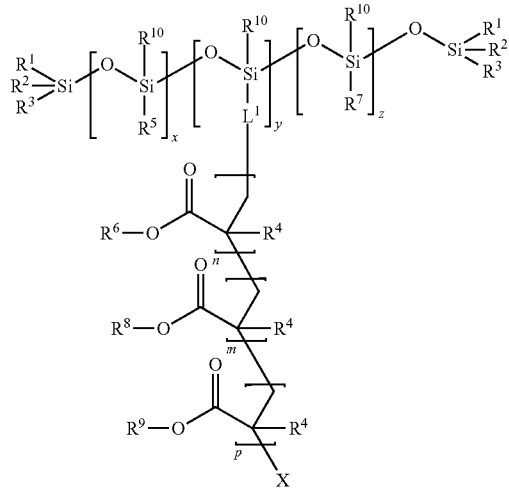

wherein x is an integer from 0 to 100;
y is an integer from 1 to 100;
z is an integer from 0 to 100;
x+y+z is at least 5
n is an integer from 0 to 50;
m is an integer from 0 to 50;
p is an integer from 0 to 50;
X is a halide;
$L^1$ is a linking group;
$R^1$, $R^2$, $R^3$ and $R^{10}$ are independently $C_1$-$C_{10}$ alkyl, cyclopentyl, cyclohexyl, benzyl, toluoyl, xylyl or phenyl;
$R^4$ is hydrogen, $C_1$-$C_{10}$ alkyl, cyclopentyl, cyclohexyl, benzyl, toluoyl, xylyl, phenyl;
$R^5$ is $C_1$-$C_{10}$ alkyl, cyclopentyl, cyclohexyl, benzyl, toluoyl, xylyl, phenyl, or a cross linking group;
$R^7$ is hydrogen, $C_1$-$C_{10}$ alkyl, cyclopentyl, cyclohexyl, benzyl, toluoyl, xylyl, phenyl, or a cross linking group;
$R^6$, $R^8$, and $R^9$ are independently a biocidal group that is toxic to organisms that cause fouling in an aquatic environment; a fouling release group; a texturizing group; or combination thereof. At least one of n, m, or p is not 0. The biocidal group may include a triclosan moiety.

In such a cross linked copolymer R4 and R10 are typically methyl. The polysiloxane copolymer is commonly a random copolymer and the graft polymethacrylate (co)polymer chain which is grafted onto the polysiloxane copolymer is typically a block (co)polymer. At least one of R6, R8, and R9 typically includes an alkoxy alkyl group, such as a methoxy ethyl group or a polyalkoxy alkyl group. One or more of R6, R8, and R9 may includes a biocidal group. At least one of R6, R8, and R9 may be:

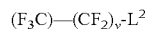

wherein v is an integer from 1 to 25; and L2 is a linking group. The L2 linker may be an ethylene group, a methylene group or a combination thereof. X is commonly Cl, Br or a combination thereof. The polyamine may include a diamine, e.g., 1,4-diaminobutane, bis(dimethylamino)-dimethylsilane, 1,3-dipyridyl propane, 1,3-bis(N,N-dimethylamino)-butane, or combinations thereof. Other polyamines, such as N,N,N'N", N"-pentamethyl-diethylenetriamine, may also be employed.

In another embodiment, the siloxane-based polymers based in the same polymeric material includes a cross linked copolymer which is prepared by cross linking a random or block copolymer using a polyamine, where the random or block copolymer has the formula:

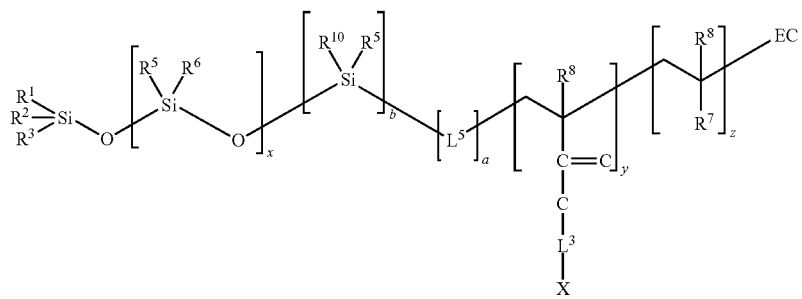

wherein x is an integer from 0 to 100;

y is an integer from 1 to 100;

z is an integer from 0 to 100;

x+y+z is at least 5 a is 0 or 1;

b is 0 or 1;

X is a halide;

EC is an end cap group;

$L^5$ and $L^3$ are linking groups;

$R^1$, $R^2$, $R^3$, $R^5$, and $R^{10}$ are independently $C_1$-$C_{10}$ alkyl, cyclopentyl, cyclohexyl, benzyl, toluoyl, xylyl or phenyl;

$R^6$ is $C_1$-$C_{10}$ alkyl, cyclopentyl, cyclohexyl, benzyl, toluoyl, xylyl, phenyl, or a cross linking group; and $R^7$ is a $C_1$-$C_{10}$ alkyl, cyclopentyl, cyclohexyl, benzyl, toluoyl, xylyl, phenyl, a group that includes a biocidal moiety that is toxic to organisms that cause fouling in an aquatic environment, a fouling release group, a texturizing group, $R^5$ is typically methyl and $R^7$ may include a another biocidal group, such as a triclosan moiety. The $L^3$ linker is commonly an alkylene group, wherein the alkylene group suitably has 2-10 carbon atoms. $L^3$-X may be a haloalkyl group, such as a 2-chloroethyl or 3-bromopropyl group. The $L^1$ linker is commonly a group such as represented by the structure:

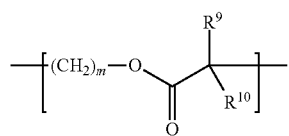

wherein $R^9$ and $R^{10}$ are independently hydrogen or lower alkyl and m is 2 to 6. In this type of polymeric material, the $R^7$ group may be represented by:

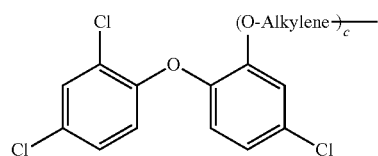

wherein c is 0 or 1 and the alkylene has 2 to 20 carbon atoms. The polyamine employed as a cross-linker may be a diamine, such as 1,4-diaminobutane, bis(dimethylamino)-dimethylsilane, 1,3-dipyridyl propane and/or 1,3-bis(N,N-dimethylamino)-butane. The polyamine may also include other amines, such as N,N,N',N'',N''-pentamethyl-diethylenetriamine.

In another embodiment, an anticrobial material comprising a first polymer cross linked with a second polymer using an ionene bridge is provided. The first polymer and/or the second polymer comprise a polysiloxane polymer segment. At least one of the first and second polymers may include a pendant group selected from the group comprising a texturizing group, a fouling release group, a biocidal group, or a mixture thereof. The pendant group may include a fluorocarbon is coupled to the first polymer, the second polymer, and/or the ionene bridge.

In yet another embodiment, the polyamine cross-linked polysiloxane may include cross-linked copolymer which is prepared by cross-linking a copolymer using a polymine, wherein the copolymer has the formula:

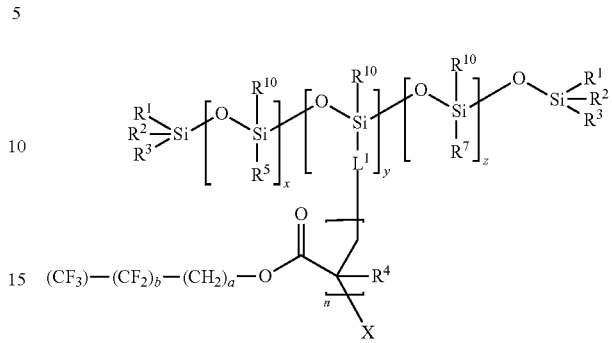

wherein x is an integer from 0 to 100;

y is an integer from 1 to 100;

z is an integer from 0 to 100;

x+y+z is at least 10;

n is an integer from 1 to 50;

a is 1, 2, or 3;

b is an integer from 1 to 15;

X is Cl and/or Br;

$L^1$ is a linking group;

$R^1$, $R^2$, $R^3$, and $R^{10}$ are independently $C_1$-$C_{10}$ alkyl, cyclopentyl, cyclohexyl, benzyl, toluoyl, xylyl or phenyl;

$R^4$ is hydrogen, $C_1$-$C_{10}$ alkyl, cyclopentyl, cyclohexyl, benzyl, toluoyl, xylyl, phenyl;

$R^5$ is $C_1$-$C_{10}$ alkyl, cyclopentyl, cyclohexyl, benzyl, toluoyl, xylyl, phenyl, or a cross linking group; and $R^7$ is hydrogen, $C_1$-$C_{10}$ alkyl, cyclopentyl, cyclohexyl, benzyl, toluoyl, xylyl, phenyl, or a cross linking group.

In the polymeric material of embodiment F, the trialkoxysilyl functionalized quaternary amine may include a compound of the formula:

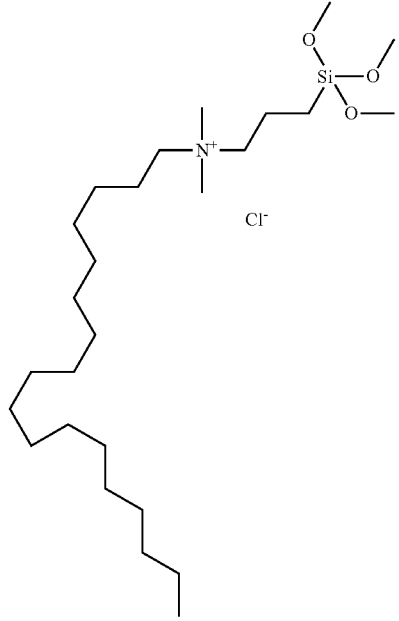 [SMILES: CCCCCCCCCCCCCCCCCC[N+](C)(C)CCC[Si](OC)(OC)OC ; [Cl-]]

In the coated substrate of embodiment E, the polymeric material may be prepared by reacting a mixture that can comprise silanol terminated polysiloxane and quaternary aminosiloxane of the following formula (wherein R is an alkyl group having 10 to 25 carbon atoms and, more desirably, is an n-alkyl group 12 to 20 carbon atoms):

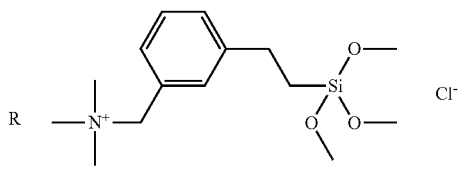

In the coated substrate of embodiment E, the polymeric material can be prepared by reacting a mixture that may comprise silanol terminated polysiloxane; and quaternary aminosiloxane of the following formula (wherein R is an alkyl group having 10 to 25 carbon atoms and, more desirably, is an n-alkyl group 12 to 20 carbon atoms):

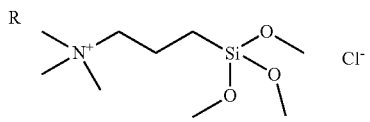

In the polymeric material of embodiment F, the trialkoxysilyl functionalized quaternary amine can include a compound of the formula:

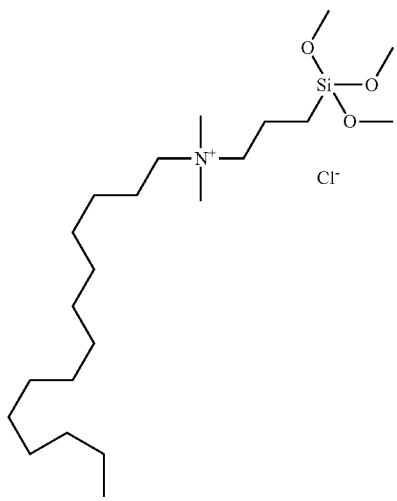 [SMILES: CCCCCCCCCCCCCC[N+](C)(C)CCC[Si](OC)(OC)OC ; [Cl-]]

In another embodiment, a polymeric material (Q) may include quaternary amino functionalized cross-linked polysiloxane.

In another embodiment, the polymeric material (R) can include the quaternary amino functionalized cross-linked polysiloxane prepared by reacting a mixture which includes alkoxysilyl functionalized quaternary amine and silanol terminated polysiloxane. In the polymeric material of embodiment R, the mixture can further comprise alkyltriacyloxysilane. In the polymeric material of embodiment R, the mixture may further comprise a tetra-functional acyloxysilane and/or alkoxysilane. In the polymeric material of embodiment R, the mixture may further comprise a trifunctional silane in which the reactive functionality is selected from the group that can consist of alkoxysilane, acyloxysilane, silazane, halosilane, and ketoxime-based silane. In the polymeric material of embodiment R, the mixture further comprises a tetra-functional silane in which the reactive functionality may be selected from the group consisting of alkoxysilane, acyloxysilane, silazane, halosilane, and ketoxime-based silane.

In another embodiment, the polymeric material (S) may include quaternary amino functionalized cross-linked polysiloxane, which may be prepared by reacting a mixture which can include silyl functionalized quaternary amine and polysiloxane with reactive terminal groups. In the polymeric material of embodiment S, the silyl functionalized quaternary amine can include a reactive functionality selected from the group that may consist of alkoxysilane, acyloxysilane, silazane, halosilane, and ketoxime-based silane. In the polymeric material of embodiment S, the polysiloxane with reactive terminal groups may include reactive functionality selected from the group that may consist of alkoxysilane, acyloxysilane, silazane, halosilane, and ketoxime-based silane.

Another embodiment provides a method (T) of facilitating biofilm removal on a substrate surface, comprising coating the surface with a polymeric material that includes an amino functionalized cross-linked polysiloxane, prepared by reacting a mixture, which may include alkoxysilyl functionalized quaternary amine, silanol terminated polysiloxane and alkyltriacyloxysilane. In the method of embodiment T, the alkoxysilyl functionalized quaternary amine can include trialkoxysilyl functionalized quaternary amine having an N—(C16-C20)-n-alkyl-N,N-dimethylamino group. In the method of embodiment T, the polymeric material may be formed from a mixture comprising at least about 0.01 moles and, more desirably, at least about 0.02 moles of alkoxysilyl functionalized quaternary amine per 100 gm of the silanol terminated polysiloxane. In the method of embodiment T, the silanol terminated polysiloxane may have a molecular weight of no more than about 35,000. In the method of embodiment T, the polymeric material may be formed from a mixture comprising at least about 0.01 moles and, more desirably, at least about 0.02 moles of alkoxysilyl functionalized quaternary amine per 100 gm of the silanol terminated polysiloxane; the alkoxysilyl functionalized quaternary amine may include trimethoxysilyl functionalized quaternary amine having an N—(C18)-n-alkyl-N,N-dimethylamino group, and the silanol terminated polysiloxane may have a molecular weight of about 10,000 to 30,000.

In the polymeric material (U), the alkoxysilyl functionalized quaternary amine may include a N,N-bis(trialkoxysilylalkyl)-N,N-dialkylamine. In the polymeric material, the alkoxysilyl functionalized quaternary amine may include a N,N-bis(trialkoxysilylalkyl)-N,N-dialkylamine where the trialkoxysilylalkyl group commonly comprises a suitably substituted lower alkyl group, preferably C2-C6. In the polymeric material, the N,N-bis(trialkoxysilylalkyl)-dialkylamine may include a N,N-bis(trialkoxysilylalkyl)-dialkylamine, where the trialkoxysilylalkyl comprises a suitably substituted lower alkyl group, preferably C2-C6, which is often a linear alkyl group. In the polymeric material, the N,N-bis(trialkoxysilylalkyl)-dialkylamine may include an N,N-bis(n-trialkoxysilylalkyl)-N—(C4-C15)-alkyl-alkylamine. In the polymeric material, the N,N-bis(trialkoxysilylalkyl)-dialkylamine may include a N,N-bis(3-trimethoxysilylpropyl)-N—(C4-C15)-n-alkyl alkylamine and/or N,N-bis(2-trimethoxysilylethyl)-N—(C4-C15)-n-alkyl alkylamine. In the polymeric material, the N,N-bis(trialkoxysilylalkyl)-dialkylamine may include a N,N-bis(3-trimethoxysilylpropyl)-N—(C4-C15)-n-alkyl-methylamine and a N,N-bis(2-trimethoxysilylethyl)-N—(C4-C15)-n-alkyl-methylamine.

One embodiment provides a polymer-based composition comprising:
 (A) amino-functional polysiloxane; and
 (B) a plurality of metal species (e.g., silver species) distributed within the polysiloxane.

Suitable amino-functional siloxane based polymers may be formed by reacting a mixture which includes alkoxysilyl functionalized quaternary amine and silanol terminated polysiloxane. Examples of suitable alkoxysilyl functionalized quaternary amines are represented by formula:

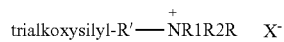

wherein R1 and R2 are lower alkyl, R' is alkylene, R is an n-alkyl group having 5 to 25 carbon atoms, and X is a halide. The mixture may also include up to about 25 wt. % and more suitably, about 5 to 15 wt. % of a filler, such as silica. In other embodiments, the mixture may also include tetra-functional silane and/or trifunctional silane.

The amino-functional polysiloxane may be a crosslinked polysiloxane, e.g., a polysiloxane formed by cross-linking a suitably functionalized polysiloxane material with a polyamine-functionalized crosslinking agent. In some embodiments, the amino-functional polysiloxane may be formed by reacting a mixture which includes alkoxysilyl functionalized quaternary amine and silanol terminated polysiloxane. The mixture may also include tetra-functional silane and/or trifunctional silane. Examples of suitable tetra-functional and trifunctional silane include acyloxysilanes (e.g., an alkyltriacyloxysilane) and/or alkoxysilanes. In other embodiments, the mixture may comprise a tetra-functional silane and/or trifunctional silane in which the reactive functionality is selected from the group consisting of silazane, halosilane, and ketoxime-based silane.

In certain embodiments, the cross-linked polysiloxane may be prepared by cross-linking a copolymer using a polyamino functionalized material, wherein the copolymer has the formula:

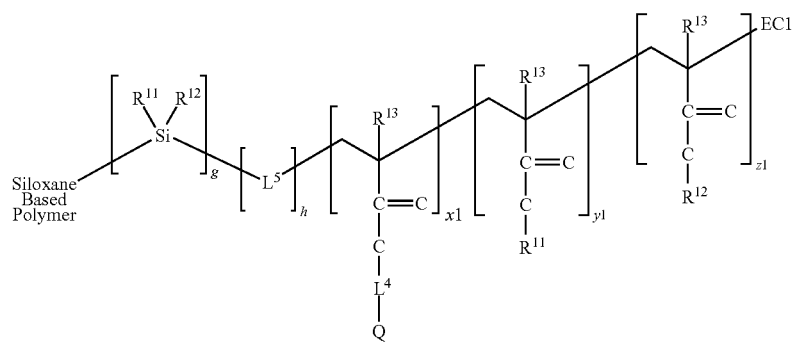

x1 is an integer from 0 to 100;
y1 is an integer from 0 to 100;
z1 is an integer from 0 to 100;
g is 0 or 1;
h is 0 or 1;
at least one of x1, y1, or z1 is not 0;
Q is a halide or an end cap group;
L4 and L5 are linking groups;
R11 and R12 are independently C1-C10 alkyl, cyclopentyl, cyclohexyl, benzyl, toluoyl, xylyl or phenyl;
R5 is C1-C10 alkyl, cyclopentyl, cyclohexyl, benzyl, toluoyl, xylyl or phenyl or a cross linking group;
R13 is an H and/or C1-C10 alkyl;
R11 and R12 include independently a biocidal group that is toxic to organisms that cause fouling in an aquatic environment; a fouling release group; a texturizing group; or combination thereof In other embodiments, the cross-linked polysiloxane may be prepared by cross linking a copolymer using a polyamine, wherein the copolymer has the formula:

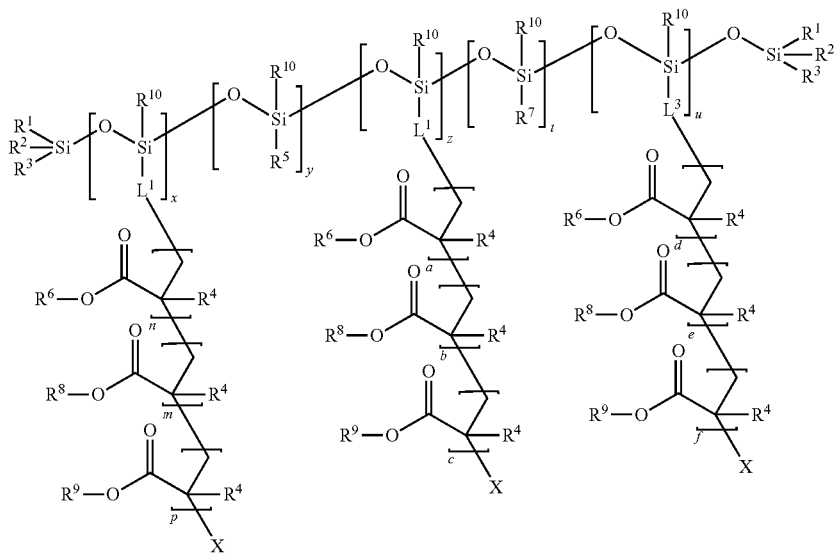

wherein x is an integer from 0 to 100;
y is an integer from 0 to 100;
z is an integer from 0 to 100,
t is an integer from 0 to 100;
u is an integer from 0 to 100;
x+y+z+t+u is at least 5;
at least one of u, x and z is not zero;
n is an integer from 0 to 50;
m is an integer from 0 to 50;
p is an integer from 0 to 50;
a is an integer from 0 to 50;
b is an integer from 0 to 50;
c is an integer from 0 to 50;
d is an integer from 0 to 50;
e is an integer from 0 to 50;
f is an integer from 0 to 50;
at least one of n, m, p, a, b, c, d, e and f is not zero;
X is a halide or an end cap group;
Y is a halide or an end cap group;
Z is a halide or an end cap group;
$L^1$, $L^2$, and $L^3$ are linking groups;
$R^1$, $R^2$, $R^3$, and $R^{10}$ are independently $C_1$-$C_{10}$ alkyl, cyclopentyl, cyclohexyl, benzyl, toluoyl, xylyl or phenyl;
$R^4$ is hydrogen, $C_1$-$C_{10}$ alkyl, cyclopentyl, cyclohexyl, benzyl, toluoyl, xylyl, or phenyl;
$R^5$ is $C_1$-$C_{10}$ alkyl, cyclopentyl, cyclohexyl, benzyl, toluoyl, xylyl, phenyl, or a cross linking group;
$R^7$ is hydrogen, $C_1$-$C_{10}$ alkyl, cyclopentyl, cyclohexyl, benzyl, toluoyl, xylyl, phenyl, or a cross linking group;
R6, R8, and R9 include independently a biocidal group that is toxic to organisms that cause fouling in an aquatic environment; a fouling release group; a texturizing group; or combination thereof.

An embodiment provides a method of forming an antimicrobial coating which includes:
forming a coating layer on the surface of a substrate;
wherein the coating layer includes amino-functional polysiloxane; and
exposing the coating layer to a solution containing metal species.

The amino-functional polysiloxane commonly includes quaternary ammonium groups, e.g., tetraalkyl ammonium groups. Examples of suitable metal species which may be incorporated into the coating via this method include silver, zinc, cadmium, mercury, antimony, gold, aluminum, copper, platinum, titanium and/or palladium species. The amino-functional polysiloxane may include polymer formed by reacting a mixture which includes alkoxysilyl functionalized quaternary amine and silanol terminated polysiloxane. Such a reaction mixture may also include tetra-functional silane and/or trifunctional silane (e.g., an alkyltriacyloxysilane). Such a reaction mixture may also include also include a filler, such as silica. For example, in certain embodiments, the reaction mixture may also include up to about 25 wt. % and, more suitably about 5 to 15 wt. % silica.

It will be readily apparent to one skilled in the art that varying substitutions and modifications may be made to the invention disclosed herein without departing from the scope and spirit of the invention. The invention illustratively described herein suitably may be practiced in the absence of any element or elements, limitation or limitations which is not specifically disclosed herein. The terms and expressions which have been employed are used as terms of description and not of limitation, and there is no intention that in the use of such terms and expressions of excluding any equivalents of the features shown and described or portions thereof, but it is recognized that various modifications are possible within the scope of the invention. Thus, it should be understood that although the present invention has been illustrated by specific embodiments and optional features, modification and/or variation of the concepts herein disclosed may be resorted to by those skilled in the art, and that such modifications and variations are considered to be within the scope of this invention.

What is claimed is:
1. An antimicrobial polymer-based composition comprising:
(A) quaternary amino functionalized cross-linked polysiloxane; and
(B) an antimicrobially-effective amount of metal species distributed within the crosslinked polysiloxane;
wherein the quaternary amino functionalized cross-linked polysiloxane has a structure corresponding to a reaction product of reactants consisting essentially of
alkoxysilyl functionalized quaternary amine and tetra-functional silane and/or trifunctional silane; and silanol terminated polysiloxane having a molecular weight of about 10,000 to 75,000;

where the alkoxysilyl functionalized quaternary amine is represented the formula

in which R' is ethylene and/or propylene, $R_1$ and $R_2$ are methyl, benzyl and/or ethyl, X is chloride and/or bromide, and R is an n-alkyl group having 12 to 20 carbon atoms; and the silanol terminated polysiloxane is represented by the formula

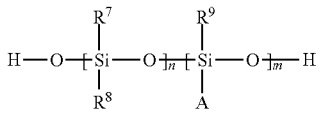

$R^7$, $R^8$, and $R^9$ are alkyl, A is alkyl and/or alkoxy, n is 0 to 5000, m is 0 to 2000, and n+m are least 10.

2. The polymer-based composition of claim 1, further comprising a plurality of metal species distributed within the crosslinked polysiloxane, wherein the metal species include silver, zinc, cadmium, mercury, antimony, gold, aluminum, copper, platinum, titanium, or palladium species, or a combination thereof.

3. The polymer-based composition of claim 1, further comprising an antimicrobial agent selected from chlorohexidine, triclosan, gramicidin, levofloxacin, polymixin, norfloxacin, sulfamylon, polyhexamethylene biguanide, alexidine, minocycline, iodine, benzalkonium chloride, or rifampicin, or a combination thereof.

4. An antimicrobial polymer-based composition comprising:

(A) quaternary amino functionalized cross-linked polysiloxane; and (B) an antimicrobially-effective amount of silver species distributed within the polysiloxane;

wherein the quaternary amino functionalized cross-linked polysiloxane has a structure corresponding to a reaction product of reactants consisting essentially of alkoxysilyl functionalized quaternary amine and tetrafunctional silane and/or trifunctional silane; and silanol terminated polysiloxane having a molecular weight of about 10,000 to 75,000;

wherein the alkoxysilyl functionalized quaternary amine is represented by the formula

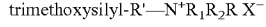

in which R' is ethylene and/or propylene, $R_1$ and R are methyl, benzyl and/or ethyl, X is chloride and/or bromide, and R is an n-alkyl group having 12 to 20 carbon atoms; and the silanol terminated polysiloxane is represented by the formula

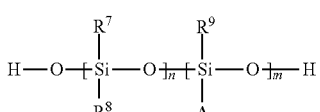

$R^7$, $R^8$, and $R^9$ are alkyl, A is alkyl and/or alkoxy, n is 0 to 5000, m is 0 to 2000, and n+m are least 10.

5. The polymer-based composition of claim 4, wherein the silver species include silver(I) ions.

6. The polymer-based composition of claim 4 wherein the silver species include silver nanoparticles.

7. The polymer-based composition of claim 4, comprising an antimicrobially-effective amount of the silver species.

8. The polymer-based composition of claim 7, wherein the silver species are in releasable form.

9. The polymer-based composition of claim 7, further comprising a second antimicrobial agent.

10. The polymer-based composition of claim 9, wherein the second antimicrobial agent comprises chlorhexidine, triclosan, gramicidin, polymixin, norfloxacin, sulfamylon, polyhexamethylene biguanide, alexidine, levofloxacin, minocycline, iodine, benzalkonium chloride, rifampicin, or a combination thereof.

11. The polymer-based composition of claim 4, further comprising an antifungal agent.

12. The polymer-based composition of claim 4, wherein the silver species are distributed throughout the polysiloxane.

13. The polymer-based composition of claim 4, wherein the quaternary amino functionalized cross-linked polysiloxane comprises a quaternary ammonium salt of a polyamine cross-linked polysiloxane.

14. The polymer-based composition of claim 4, wherein the quaternary amino functionalized cross-linked polysiloxane is a reaction product of reactants which include alkoxysilyl functionalized quaternary amine and silanol terminated polysiloxane; and the silver species include silver nanoparticles.

15. The polymer-based composition of claim 14, further comprising a second antimicrobial agent.

16. The polymer-based composition of claim 4, wherein the silver species include silver nanoparticles.

17. The polymer-based composition of claim 4, wherein the composition further comprises a plurality of additional metal species distributed within the crosslinked polysiloxane, wherein the additional metal species include zinc, cadmium, mercury, antimony, gold, aluminum, copper, platinum, titanium or palladium species, or a combination thereof.

18. The polymer-based composition of claim 1, wherein the silanol terminated polysiloxane comprises silanol terminated polydimethylsiloxane and the reactants contain at least 0.015 moles of the alkoxysilyl functionalized quaternary amine per 100 gm of the silanol terminated polysiloxane.

19. The polymer-based composition of claim 18, wherein the trialkoxysilyl functionalized quaternary amine includes a quaternary N—($C_{16}$-$C_{20}$)-n-alkyl-N,N-dimethylamino group; and the composition is formed by treating the quaternary amino functionalized cross-linked polysiloxane with a solution of a soluble silver salt such that the polymer-based composition contains about 0.05 to about 0.2 wt. % of a cationic silver species.

* * * * *

UNITED STATES PATENT AND TRADEMARK OFFICE
CERTIFICATE OF CORRECTION

PATENT NO.         : 8,709,394 B2                                    Page 1 of 1
APPLICATION NO.    : 12/661902
DATED              : April 29, 2014
INVENTOR(S)        : Bret Ja Chisholm and Partha Majumdar It is certified that error appears in the above-identified patent and that said Letters Patent is hereby corrected as shown below:

IN THE CLAIMS

Column 31, line 4, claim 1, should read -- represented by the formula --.

Column 31, line 50, claim 4, should read -- $R_1$ and $\underline{R_2}$ are methyl, --.

Signed and Sealed this
Sixteenth Day of December, 2014

Michelle K. Lee
*Deputy Director of the United States Patent and Trademark Office*

UNITED STATES PATENT AND TRADEMARK OFFICE
CERTIFICATE OF CORRECTION

PATENT NO. : 8,709,394 B2
APPLICATION NO. : 12/661902
DATED : April 29, 2014
INVENTOR(S) : Chisholm et al.

Page 1 of 1

It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 901 days.

Signed and Sealed this
Twenty-first Day of July, 2015

Michelle K. Lee
*Director of the United States Patent and Trademark Office*